United States Patent [19]

van Eikeren et al.

[11] Patent Number: 5,041,227
[45] Date of Patent: Aug. 20, 1991

[54] SELECTIVE AQUEOUS EXTRACTION OF ORGANICS COUPLED WITH TRAPPING BY MEMBRANE SEPARATION

[75] Inventors: Paul van Eikeren; Daniel J. Brose; Roderick J. Ray, all of Bend, Oreg.

[73] Assignee: Bend Research, Inc.

[21] Appl. No.: 595,241

[22] Filed: Oct. 9, 1990

[51] Int. Cl.⁵ .............................................. B01D 61/00
[52] U.S. Cl. .................... 210/640; 210/651; 210/652
[58] Field of Search ............... 210/644, 648, 641, 634, 210/643, 649, 650–654, 640

[56] References Cited

U.S. PATENT DOCUMENTS

| | | | |
|---|---|---|---|
| 3,956,112 | 5/1976 | Lee et al. | 210/644 |
| 4,664,808 | 5/1987 | Kim | 210/648 |
| 4,670,151 | 6/1987 | Bitter | 210/641 |

Primary Examiner—Frank Sever
Attorney, Agent, or Firm—Chernoff, Vilhauer, McClung & Stenzel

[57] ABSTRACT

An improvement to processes for the selective extractation of organic solutes from organic solvents by water-based extractants is disclosed, the improvement comprising coupling various membrane separation processes with the organic extraction process, the membrane separation process being utilized to continuously recycle the water-based extractant and at the same time selectively remove or concentrate organic solute from the water-based extractant.

51 Claims, 21 Drawing Sheets

SELECTIVE AQUEOUS EXTRACTION OF ORGANICS COUPLED WITH TRAPPING BY MEMBRANE SEPARATION

The government has rights in this invention pursuant to Contract No. DE-AC03-87ER80467 awarded by the Department of Energy.

BACKGROUND OF THE INVENTION

The selective extraction of organic solutes from organic solvents by water on the basis of relative partitioning of the organic solute between organic and aqueous phases is known, but, as a practical matter, has been restricted to organics that exhibit high coefficients of partition in water. The principal reason for this is that the selective aqueous extraction of organics with low partition coefficients would require impractically large volumes of water, which in turn would require large energy input to evaporate the water so as to isolate the extracted organic component.

European Patent Application No. 0 329 347 discloses the extraction of cholesterol from melted butter or oil with a methanol/water mixture containing 1-2 wt % water. Following extraction, the methanol/water mixture was cooled, then distilled to provide resuable methanol/water extractant. In addition to solvent recovery by distillation, the same Application discloses solvent recovery by passage through a loose RO membrane. However, there is no disclosure or suggestion of coupling the solvent recovery step with the extraction step nor of any efficiencies which might be realized from such a coupling.

The present invention overcomes the inherent limitations of aqueous extraction of organics, allowing selective extraction of organic solutes with low coefficients of partition in water, providing a means of trapping or concentrating such low-partitioning organic solutes, and allowing recycling of extractant.

SUMMARY OF THE INVENTION

The present invention comprises an improvement to any process for the extraction of organic solutes from an organic solvent or from an organic solvent mixture with an aqueous-based extractant, the basic improvement comprising continuously recycling said aqueous-based extractant through a membrane separation process that selectively removes the organic solute from the extractant, the membrane separation process being selected from at least one of reverse osmosis, nanofiltration, ultrafiltration, pervaporation, membrane distillation, membrane contactors, and supported-liquid membrane. By "aqueous-based extractant" is meant a liquid extractant comprising water, water and water-miscible liquid complexing agent(s), or water containing one or more soluble complexing agents.

DETAILED DESCRIPTION OF THE INVENTION

According to the present invention, there is provided a significant improvement to organic/aqueous extraction processes whereby organic solutes are selectively extracted from organic solvents with water which may contain water-soluble or water-miscible complexing agent, the extraction taking place on the basis of relative partitioning of the organic solute between organic and aqueous phases. The basic improvement lies in the continuous recycling of the aqueous-based extractant through a membrane separation process that selectively removes the organic solute from the extractant, wherein the membrane separation process is selected from reverse osmosis, pervaporation, membrane contactor and supported-liquid membrane. Additional efficiencies may be realized by partially combining the organic solute-rich product of said membrane separation process with the organic solute-rich extraction water of said organic/aqueous extraction process to form the feed to said membrane separation process. Such improvements permit the selective extraction of the organic solute of interest with the use of a relatively small amount of water, and further allow such extraction of organic solutes with low coefficients of partition in water, permitting the recovery and reuse of the organic solvents of concern.

The invention is useable with virtually any organic/aqueous extraction system, whether such systems are membrane-based or not, including all types of liquid/liquid extractors, whether the phases contact each other by gravity or by centrifugal force, and whether a water-soluble or water-miscible complexing agent is present in the aqueous phase. A good summary of the types of liquid/liquid extractors that are useable in the present invention, which is incorporated herein by reference, is found in the *Handbook of Separation Techniques for Chemical Engineers*, §1.10 (Schweitzer ed. 1979). Examples of membrane-based organic/aqueous extraction systems with which the present invention is useable include ultrafiltration ("UF"), nanofiltration, supported liquid membranes ("SLM"), and membrane contactors ("MC").

The improved process is best understood by referring to the schematic drawings.

Figure 1:
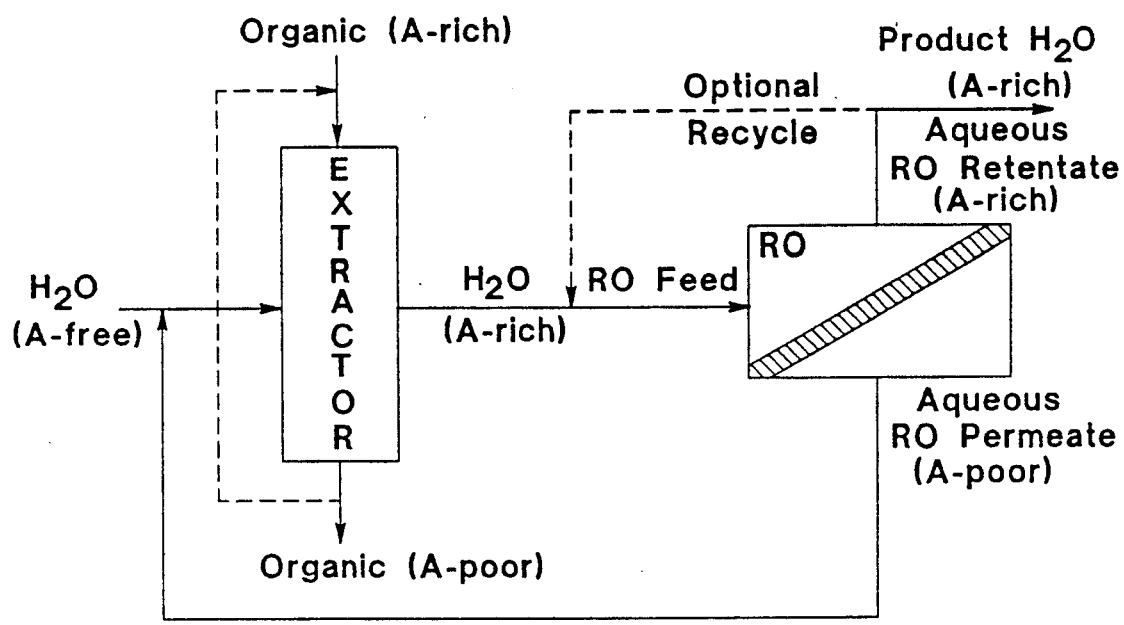
FIGS. 1-20 are all schematic drawings illustrating exemplary embodiments of the present invention; auxiliary equipment, such as pumps and valves, is not shown in every case.
Figure 2:
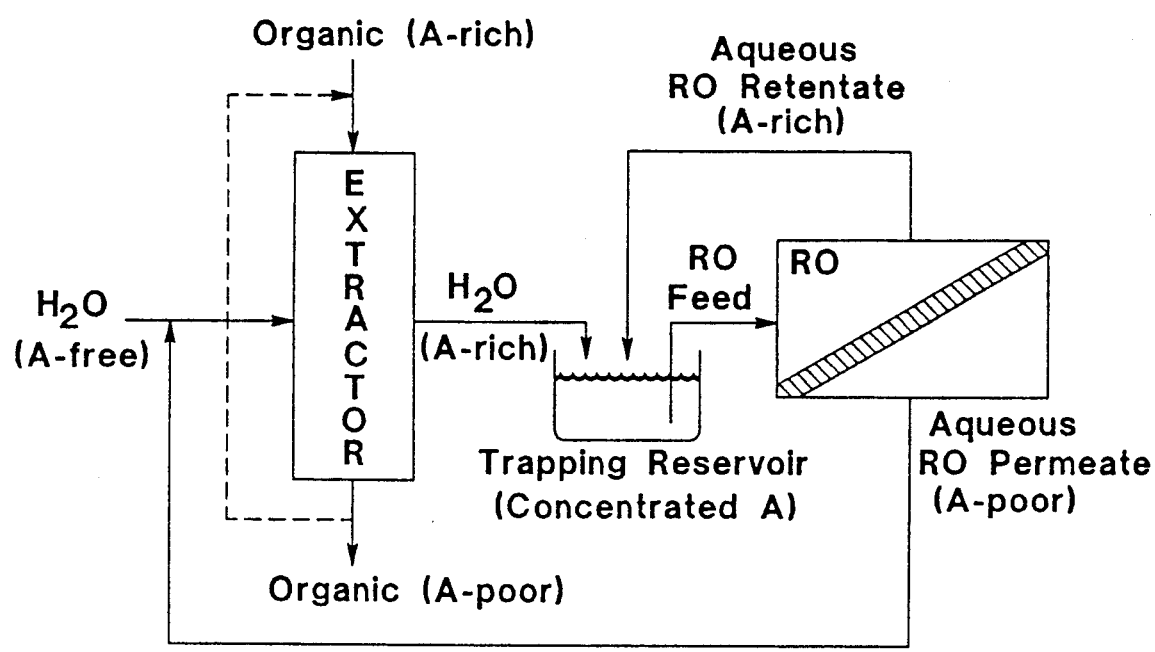

FIG. 1 shows the hypothetical simple case of a liquid/liquid extractor coupled with a reverse osmosis membrane to extract organic solute A with water from an organic solvent, on the basis of solute A's relative partitioning between water and the organic solvent. There, a feed stream comprising A-free water and water having a relatively lower concentration of A ("A-poor $H_2O$") is shown entering from the left into a liquid/liquid extractor, an organic solvent stream having a relatively higher concentration of A ("A rich") is shown entering the top of the liquid/liquid extractor, whereby solute A is partially extracted with water, and is shown leaving the liquid/liquid extractor to the right as A-rich $H_2O$, and comprising a portion of the feed ("RO feed") to a reverse osmosis membrane separator ("RO"). The water extraction of solute A leaves behind an organic solvent portion with a relatively lower concentration of A, shown leaving the bottom of the liquid/liquid extractor as A-poor organic, which can be recycled back to the organic feed as shown by the dotted lines. Water permeates the RO membrane, leaving an RO retentate relatively rich in solute A concentration, which is optionally partially combined with A-rich water from the liquid/liquid extractor to form the balance of the RO feed. The A-poor RO permeate, comprising water with a relatively low concentration of solute A, is recycled to the liquid/liquid extractor to again function as extraction water. The net result of such a separation scheme is a concentration of solute A, illustrated schematically as the A-rich product H$_2$O taken off as a bleed stream from the RO retentate. Such a concentrated stream may be completely recycled and further concentrated, as shown in FIG. 2, for example, which shows the use of a trapping reservoir to trap a concentrated solution of solute A.

As will be illustrated in the Examples which follow, the improvement of the present invention permits much more efficient separation than would otherwise be realized without the use of the improvements. Such efficiency is reflected in several ways: (1) greater absolute separation; (2) greater extraction for a given membrane surface area; or (3) the same extraction with less membrane surface area.

Figure 3:
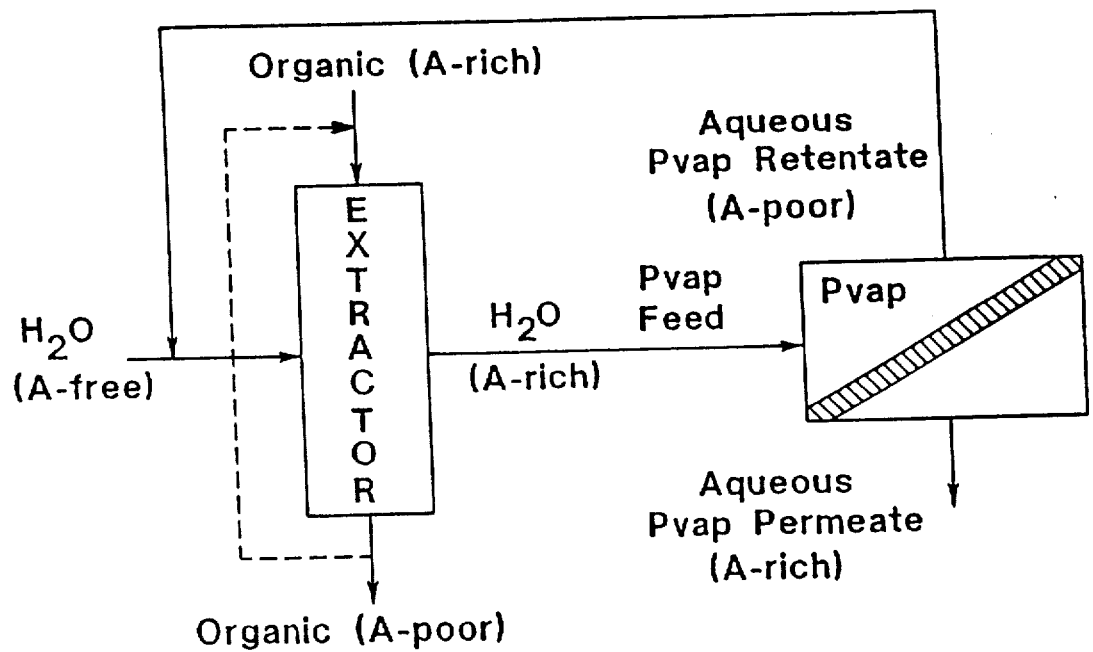

FIG. 3 illustrates essentially the same aspect of the invention as does FIG. 1, with the exception that the reverse osmosis membrane separator has been replaced with a pervaporation membrane separator ("Pvap"). In this case, solute A permeates the Pvap membrane leaving a retentate relatively low in solute A concentration which is recycled back to the liquid/liquid extractor to again function as extraction water. The Pvap permeate contains A-rich water and is the product stream.

Figure 4:
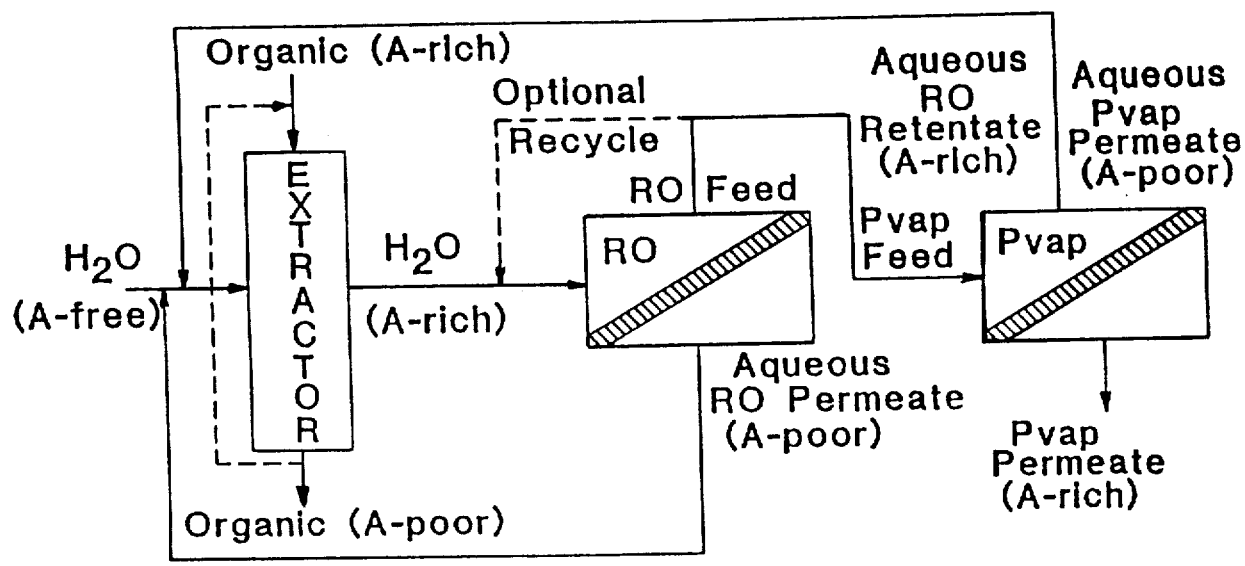

FIG. 4 illustrates an additional embodiment of the present invention where membrane separation processes have been combined to realize the efficiencies available with the present invention. In this application, the A-rich RO retentate forms the feed for a downstream Pvap membrane separation where the Pvap permeate has a higher A concentration than the RO retentate stream. Both the RO permeate and the Pvap retentate are recycled back to the liquid/liquid extractor to again function as extraction water.

Figure 5:
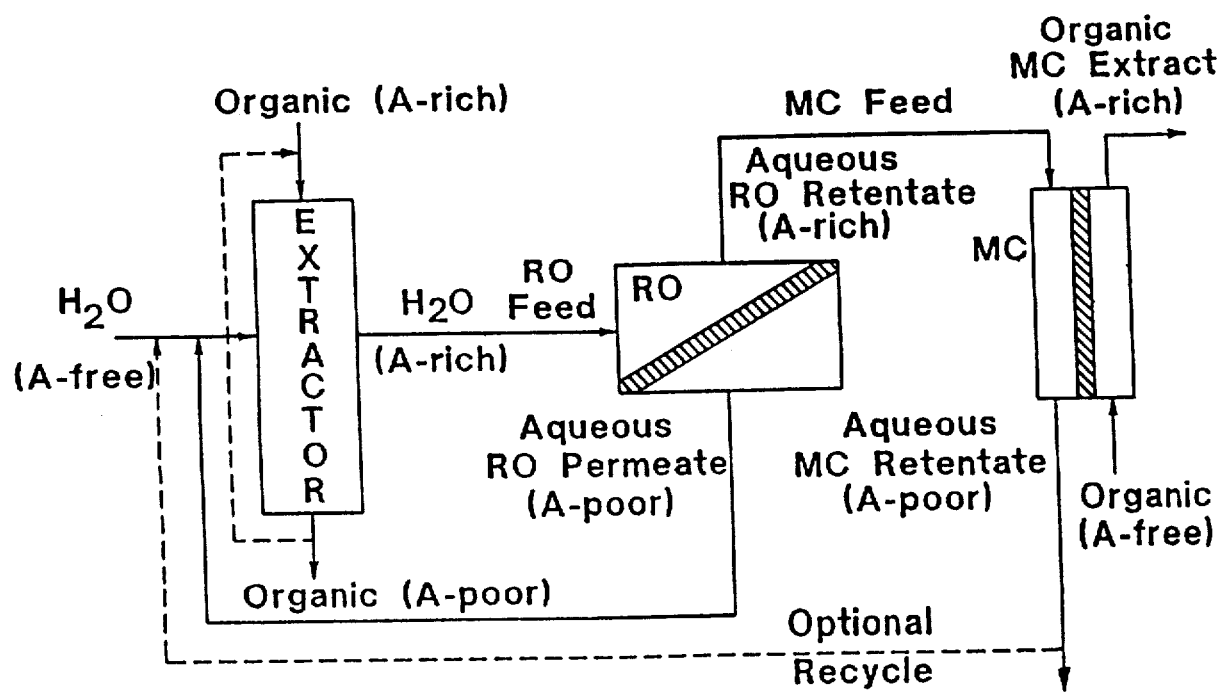

FIG. 5 illustrates essentially the same aspect of the present invention as does FIG. 4, with the exception that the pervaporation membrane separation has been replaced with a membrane contactor ("MC"). In this case, the A-rich RO retentate forms the MC feed. Solute A permeates the MC membrane leaving an MC retentate stream relatively low in solute A concentration that is recycled back to the liquid/liquid extractor along with the A-poor RO permeate to function as extraction water. Pure organic solvent that is free from solute A forms the MC solvent stream and is enriched in solute A as A permeates the MC membrane. The A-rich organic MC extract is the product stream.

Figure 6:
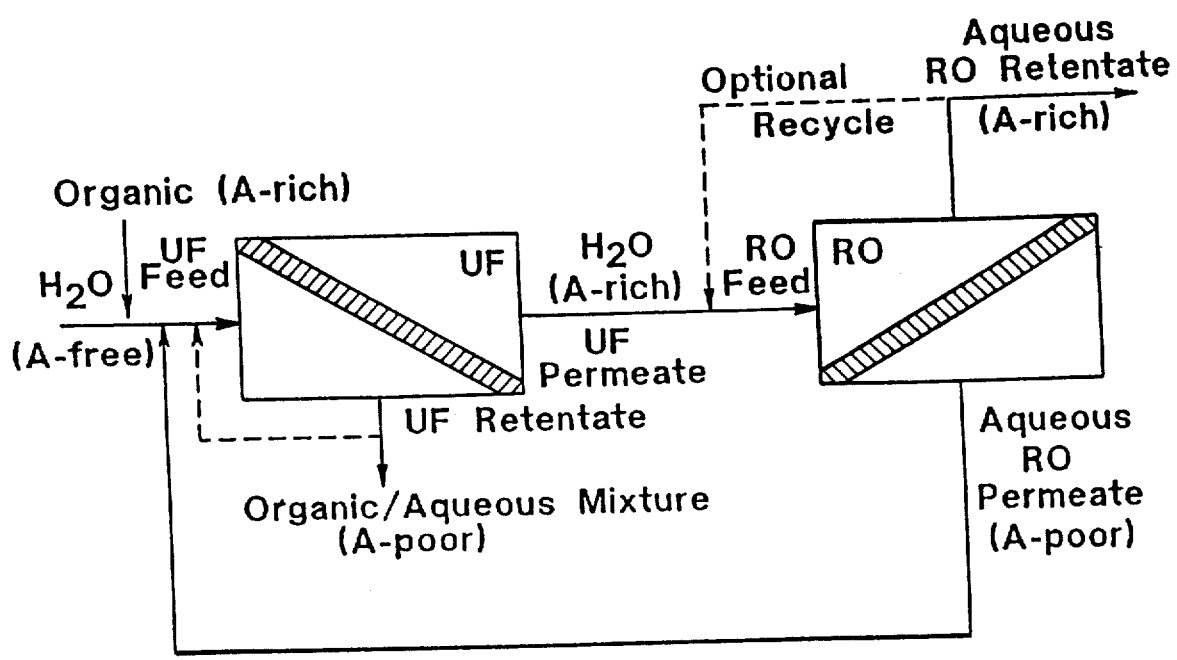

FIG. 6 illustrates essentially the same aspect of the present invention as FIG. 1, with the exceptions that the underlying organic/aqueous extraction is performed with an ultrafiltration ("UF") membrane and the organic solvent-rich ("A-poor") UF retentate is bled off to permit solvent recovery as well. Solute A and water permeate the UF membrane to form a permeate that is relatively rich in solute A, which forms the RO feed. The concentrated A-rich RO retentate can either be tapped or recycled back to the RO feed where it can be trapped. The A-poor RO permeate is recycled back to the UF feed.

Figure 7:
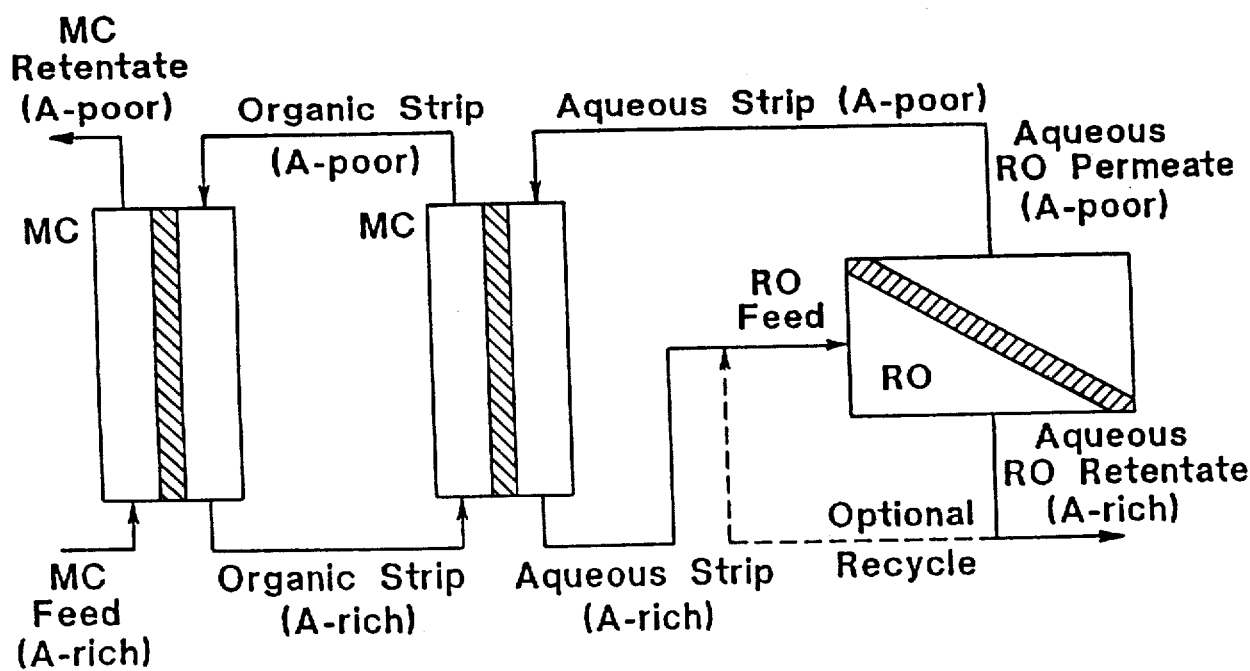

FIG. 7 illustrates an alternative embodiment to the present invention where two membrane contactors are used to perform the organic/aqueous extraction. A-rich water forms the feed for the left hand "loading" membrane contactor. An organic stream is recirculated between the loading MC and the right hand "stripping" MC. Solute A from the MC feed permeates the loading MC to form an A-rich loaded organic strip which then forms the feed for the stripping MC. A-poor water from the RO permeate forms the aqueous strip for the stripping MC. Solute A from the loaded organic strip permeates the stripping MC to form a loaded aqueous strip, which then forms the RO feed. The A-rich RO retentate can either be tapped or recycled back and combined with the loaded aqueous strip to form the RO feed to be trapped.

Figure 8:
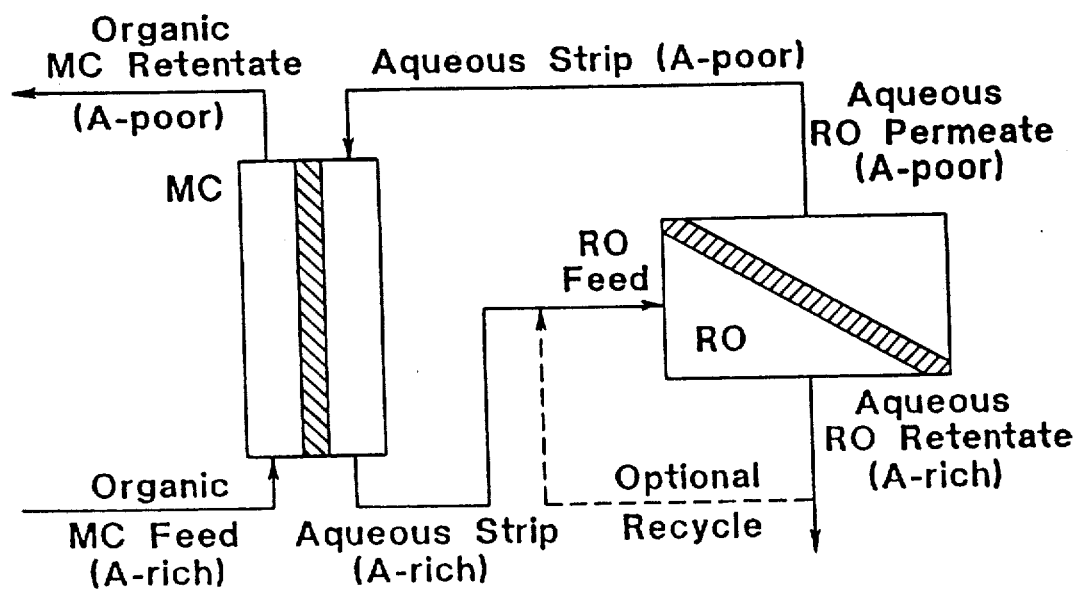

FIG. 8 illustrates a variation of FIG. 7 where one MC is used instead of two. In this case, A-rich organic forms the MC feed and A-poor RO permeate forms the unloaded aqueous strip. Solute A permeates the MC membrane to form the loaded aqueous strip which then becomes the RO feed. The A-rich RO retentate can either be tapped or combined with the loaded aqueous strip to form an A-rich RO feed, thereby effectively trapping solute A.

Figure 9A:
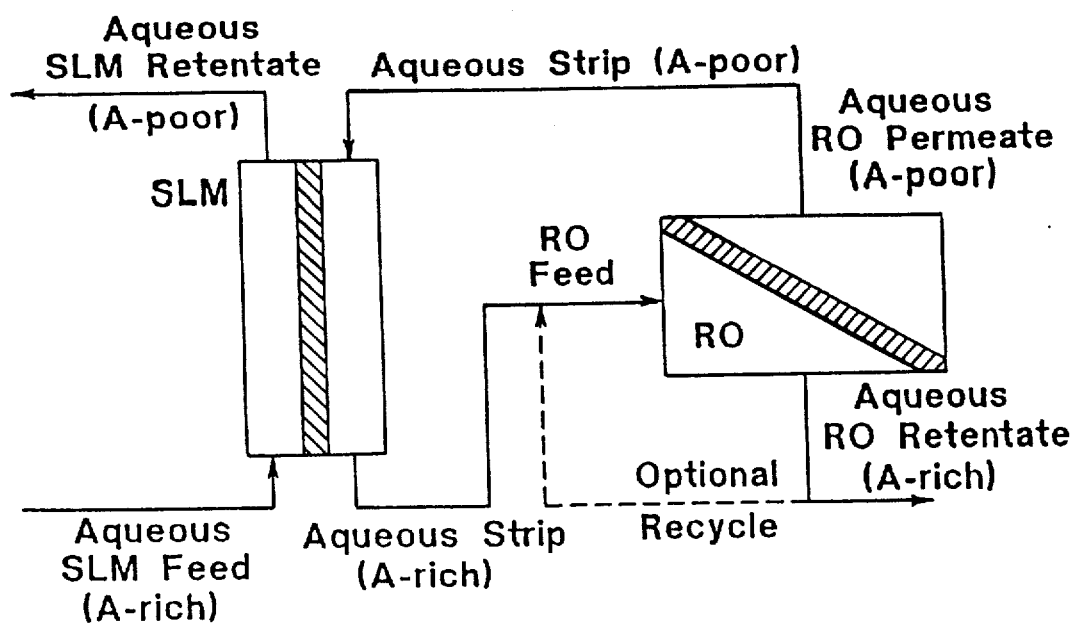

FIG. 9a illustrates another aspect of the invention wherein the extraction takes place by means of a supported liquid membrane ("SLM"). In this case the organic/aqueous extraction occurs in the SLM where the membrane pores are filled with organic solvent. A-rich water forms the SLM feed and A-poor water from the RO permeate forms the unloaded aqueous strip. Solute A permeates the SLM membrane and forms the loaded aqueous strip. The A-rich RO retentate can either be tapped or recycled back and combined with the loaded strip to form A-rich RO feed, thereby effectively trapping solute A.

Figure 9B:
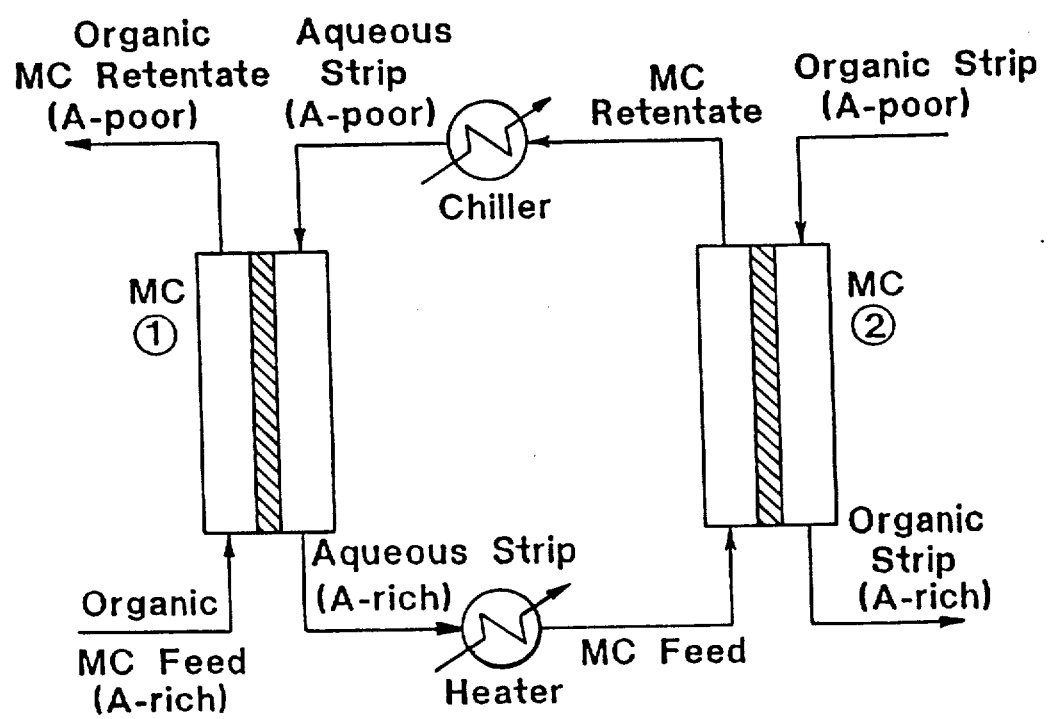

FIG. 9b illustrates a similar aspect of the invention to that shown in FIG. 8, except that the RO membrane has been replaced with a membrane contactor (MC) and heating and cooling means are incorporated in the recirculating aqueous stream. In this case, A-rich organic forms the MC feed and A-poor aqueous retentate from the second MC forms the aqueous strip to the first MC. Solute A permeates the MC membrane, which operates at a temperature different from the second MC (in this case a cooler temperature), to form the loaded aqueous strip, which then becomes the feed to the second MC. The loaded aqueous stream is heated prior to being fed to the second MC. In the second MC, solute A permeates the membrane and partitions into the organic strip solution to form the loaded organic strip stream. The aqueous A-poor retentate from the second MC is cooled and recycled to the first MC. The A-rich organic strip from the second MC is the product stream.

FIGS. 10-20 are schematics of the working examples herein.

It should be understood that selection of the particular membranes useful in the present invention is not limited to those specifically mentioned herein, but may comprise any membranes known to be useful in the particular component processes, so long as they are compatible with the particular separations to which they are applied.

Table I comprises a listing of exemplary membranes suitable in the practice of the present invention. Table II comprises a summary of the hybrid separation systems described in the Examples which follow, including the separations achieved. Analysis of the concentrations of solute and solvent in feed, concentrate and other streams was conducted either by gas chromatography or high pressure liquid chromatography. In all of the Examples wherein pressure is specified, the units are in gauge pressure.

TABLE I

| Membrane Type | Name and Source | Description |
|---|---|---|
| RO | SW-30 (Filmtec Corp., Minneapolis, MN) | spiral would polyamide thin-film composite |
| RO | AFC 99 (Paterson Candy, Whitechurch, Hampshire, U.K.) | tubular polyamide thin-film composite approx. 1.2 cm diameter |
| Pvap MC SLM | Celgard X20/2400 (Hoechst Celanese, Charlotte, NC) | microporous polypropylene hollow fibers approx. 400 microns ID/flat sheet 25 microns thick, both with 0.02 micron pore diameter |
| MC | CF 15-11 (Travenol Laboratories, Deerfield, IL) | hollow fiber module of hydrophilic regenerated cellulose |
| MC | Enka B1 Enka AG, Wuppertal, West Germany | hydrophilic regenerated cellulose hollow fibers |
| Pvap | Pebax 3533 (Atochem, S.A., Birdsboro, PA) | polyether-polyamide block copolymer film approx. 25 microns thick |
| UF | ACN 620 (Paterson Candy) | tubular polyacrylonitrile approx. 1.2 cm diameter with M.W. cutoff of 25,000 |

TABLE II

| Example No. | Separation Process | Solute of Interest | Feed Composition |
|---|---|---|---|
| 1 | UF RO | orange oil oxygenates | Cal. orange oil contg. 11 g/L oxygenates |
| 2 | MC RO | oxygenates | Cal. orange oil contg. 100 g/L oxygenates |
| 3 | MC RO | (S)-Norbornenol | products from enz. acylation of (R, S)-Norbornen-2-ol contg. 33.1 g Norbornenol |
| 4 | MC RO | (S)-phenethyl alcohol | products from enz. acylation of (R, S)-1-phenethyl alcohol with proprionic acid contg. 17 g phenethyl alcohol |
| 5 | MC MC RO | dipeptide | enz. synthesis reaction contg. 1.45 g/L dipeptide |
| 6 | MC MC RO | citric acid | fermentation beer contg. 200 g citric acid |
| 7 | SLM RO | dipeptide | enz. synthesis reaction contg. 1.45 g/L dipeptide |
| 8 | MC Pvap | orange oil oxygenates | Cal. orange oil contg. 15 g/L |
| 9 | MC Pvap | para-xylene | para-xylene in an organic solvent |
| 10 | UF RO MC | orange oil oxygenates | Cal. orange oil contg. 12 g/L oxygenates |
| 11 | MC MC | orange oil oxygenates | Cal. orange oil contg. 12 g/L oxygenates |

EXAMPLE 1

Figure 10:
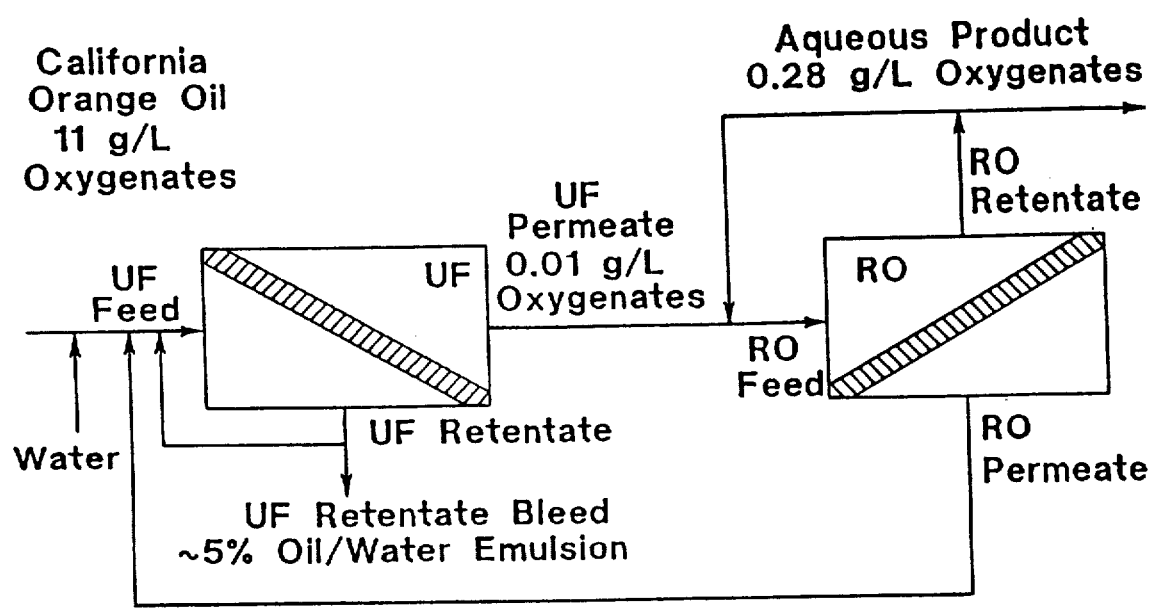

A continuous hybrid UF/RO separation system of the present invention is shown schematically in FIG. 10 for the extraction of the organic solute orange oil oxygenates from the organic solvent California orange oil. The UF membrane comprised a tubular membrane ACN 620 module from Paterson Candy having a surface area of 0.33 m$^2$ (9.7 ft$^2$) with a tube-side feed and a water flux of 0.73 kg/m$^2$.min (26 gfd). The RO module was a tubular membrane AFC 99 module, also from Paterson Candy, with 0.9 m$^2$ (9.7 ft$^2$) surface area, having a flux of 0.28 kg/m$^2$.min (9.9 gfd) when driven by a transmembrane pressure (TMP) of 3446 kPa (500 psi). The feed of California orange oil contained 11 g/L oxygenates and was fed with recycled and make-up water to the UF membrane at a rate of approximately 5 ml/min (0.08 gph).

The extraction was first conducted with the ultrafiltration membrane alone (not schematically shown) at a TMP of 586 kPa (85 psi) for 25 hours and yielded a steady state concentration of only 0.03 g/L oxygenates in the product stream. The extraction was then conducted coupled to the RO membrane as shown in FIG. 10, with a recycling of the solute-poor RO permeate to the UF feed, and combining the solute-rich RO retentate with the solute-rich extraction water of the UF separation, yielding an oxygenates concentrate stream of 0.28 g/L. A 5% orange oil/water emulsion was recovered by bleeding off the UF solvent-rich retentate.

EXAMPLE 2

Figure 11:
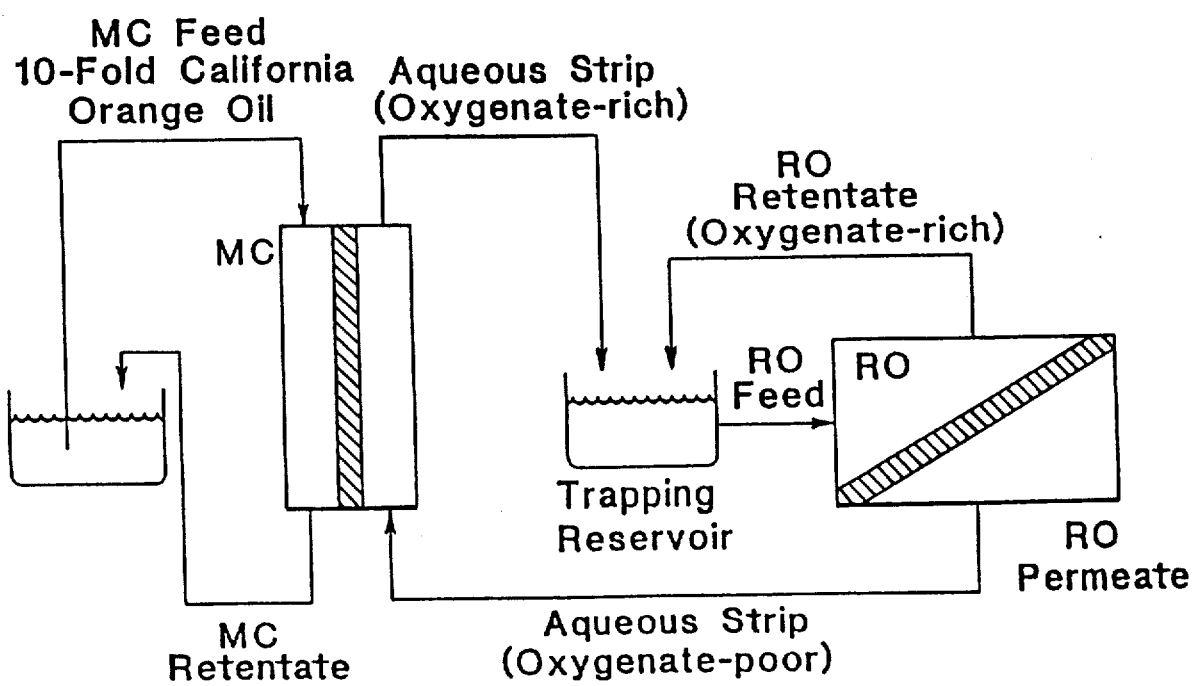

A batch hybrid MC/RO separation system is shown schematically in FIG. 11, also for the extraction of orange oil oxygenates from 10-fold California orange oil (10-fold California oil has been enriched in oxygenates over raw orange oil by a factor of 10 and contains 100 g/L oxygenates). The MC was a hollow fiber CF 15-11 dialysis module from Travenol Laboratories having a surface area of 1.1 m$^2$ (11.8 ft$^2$) with a lumen-side feed and driven by an oxygenates concentration gradient with an oxygenates permeability of 2.2×10 mg/cm$^2$.hr.g/L. The RO module was a spiral-wound SW-30 module from FilmTec having a surface area of 0.56 m$^2$ (6 ft$^2$) and an average water flux of 0.68 kg/m$^2$.min (24 gfd) when driven by a TMP of 5514 kPa (800 psi). The feed contained 10 wt % oxygenates and was fed to the MC at a rate of approximately 0.4 L/min (6.3 gph). RO permeate was recycled to the strip or aqueous side of the MC to become the MC extraction water, which was then combined in the trapping reservoir shown with the solute-rich RO retentate to form the feed to the RO module, this RO feed being fed at a rate of 7.6 L/min (120 gph).

The amount of oxygenates in the reservoir over the course of 100 minutes is shown below.

| Time (min) | Oxygenates (g) |
|---|---|
| 0 | 0 |
| 10 | 0.36 |
| 20 | 0.66 |
| 30 | 1.19 |
| 50 | 1.65 |
| 75 | 2.27 |
| 100 | 2.39 |

Using the same MC surface area, permeability and reservoir volume, the amount of oxygenates obtainable without using RO permeate water as the aqueous strip as shown in FIG. 11 was calculated as follows:

| Time (min) | Oxygenates (g) |
|---|---|
| 0 | 0 |
| 10 | 0.29 |
| 20 | 0.47 |
| 40 | 0.65 |
| 60 | 0.71 |
| 100 | 0.74 |

As is apparent, better than a three-fold increase in the amount of oxygenates was obtained with the use of RO permeate water as the aqueous strip in accordance with the invention.

EXAMPLE 3

Figure 12:
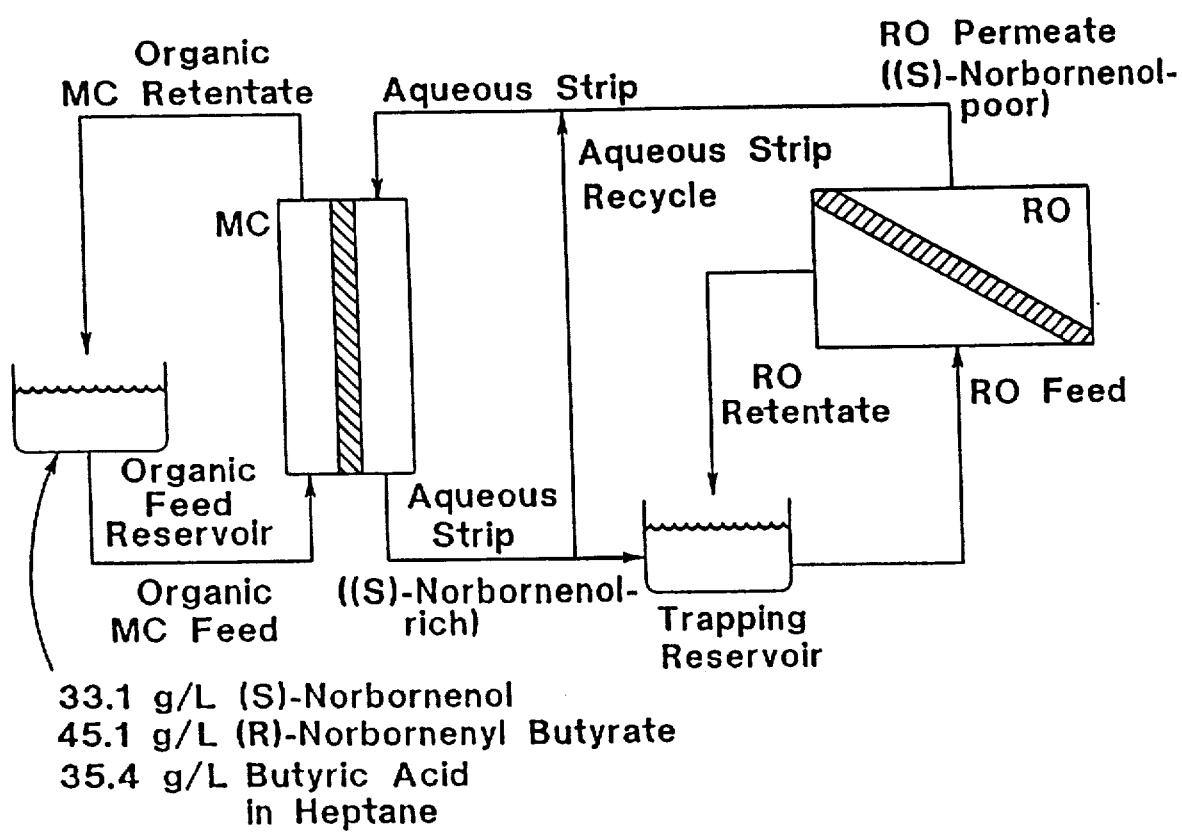

A modification of Example 2 was repeated in that different-sized membranes were used to separate (S)-Norbornen-2-ol from a feed comprising the products of the enzymatic acylation of (R,S)-Norbornen-2-ol with propionic acid, as shown in FIG. 12. Another difference from Example 2 was that part of the aqueous strip was recycled back and combined with the RO permeate to allow greater flow through the MC on the aqueous strip side. A bleed stream from the loaded aqueous strip, with the same flow rate as the RO permeate, returned to the trapping reservoir. The MC feed contained (S)-Norbornen-2-ol (Norbornenol), (R)-Norbornen-2-yl butyrate (Norbornenyl butyrate) and butyric acid in heptane, as shown in FIG. 12. Two 1.1 $m^2$ (11.8 $ft^2$) Travenol Laboratory CF 15-11 dialysis modules operating in parallel with a norbornenol permeability of 0.75 $mg/cm^2.hr.g/L$ were used as membrane contactors. The membrane in the membrane contactors retains the ester (Norbornenyl butyrate) while allowing the Norbornenol and butyric acid to permeate. The RO module, an SW-30 spiral-wound module from FilmTec having a surface area of 0.46 $m^2$ (5 $ft^2$), with a feed flow rate of 7.5 L/min (120 gph) had an average flux of 0.40 $kg/m^2.min$ (14.1 gfd) when driven by a TMP of 5514 kPa (800 psi). The MC feed, containing 33.1 g/L Norbornenol in heptane, flowed on the lumen side of the MC at a rate of 0.22 L/min (3.5 gph) RO permeate, with an average flow rate of 0.185 L/min (2.9 gph), was fed into a recirculation loop flowing at 0.54 L/rin (8.1 gph) for a total aqueous strip flow rate of 0.72 L/min (11.4 gph). A bleed stream from the loaded aqueous strip returned back to the trapping reservoir where the amount of norbcrnenol trapped steadily increased.

The amount of Norbornenol collected in the trapping reservoir over the course of 30 minutes, as well as the decrease of Norbornenol in the feed, the recovery of Norbornenol from the feed, and the purity of the feed (defined as [ester/ester+alcohol]100%) is shown in the table below.

| | Norbornenol Extraction | | | |
|---|---|---|---|---|
| Time (min) | Feed (g) | Product (g) | Feed Purity (%) | Recovery (%) |
| 0 | 33.1 | 0.0 | 58 | 0 |
| 2 | 29.3 | 3.7 | 61 | 11 |
| 4 | 12.6 | 20.5 | 78 | 62 |
| 6 | 12.6 | 20.5 | 78 | 62 |
| 8 | 9.7 | 23.4 | 82 | 71 |
| 10 | 5.7 | 27.3 | 89 | 82 |
| 15 | 2.6 | 30.4 | 95 | 92 |
| 20 | 1.5 | 31.3 | 97 | 95 |

-continued

| | Norbornenol Extraction | | | |
|---|---|---|---|---|
| Time (min) | Feed (g) | Product (g) | Feed Purity (%) | Recovery (%) |
| 30 | 0.0 | 33.1 | 100 | 100 |

Using the same MC surface area, permeability, reservoir volumes, and feed concentrations, the amount of Norbornenol extracted from the feed without the use of RO and the corresponding feed purity was calculated to be as follows:

| | Norbornenol Extraction | | | |
|---|---|---|---|---|
| Time (min) | Feed (g) | Product (g) | Feed Purity (%) | Recovery (%) |
| 0 | 33.1 | 0.0 | 58 | 0 |
| 2 | 23.7 | 9.4 | 66 | 28 |
| 4 | 15.9 | 17.2 | 74 | 52 |
| 6 | 12.3 | 20.8 | 79 | 63 |
| 8 | 10.2 | 23.0 | 82 | 69 |
| 10 | 8.3 | 24.8 | 84 | 75 |
| 15 | 6.8 | 26.3 | 87 | 79 |
| 20 | 6.3 | 26.8 | 88 | 81 |
| 30 | 6.1 | 27.0 | 88 | 82 |

As is apparent from the above data, the use of RO permeate as the aqueous strip in accordance with the present invention produces an essentially pure feed whereas without the use of RO the feed purity obtained is only 88%. The feed purity is very important, since usually only one of the enantiomers is desired, thereby making single enantiomers more valuable than a racemic mixture of the enantiomers. In this case it is desirable to have the ester stream uncontaminated by the alcohol, which, if present, results in a loss of enantiomeric purity.

EXAMPLE 4

Figure 13:
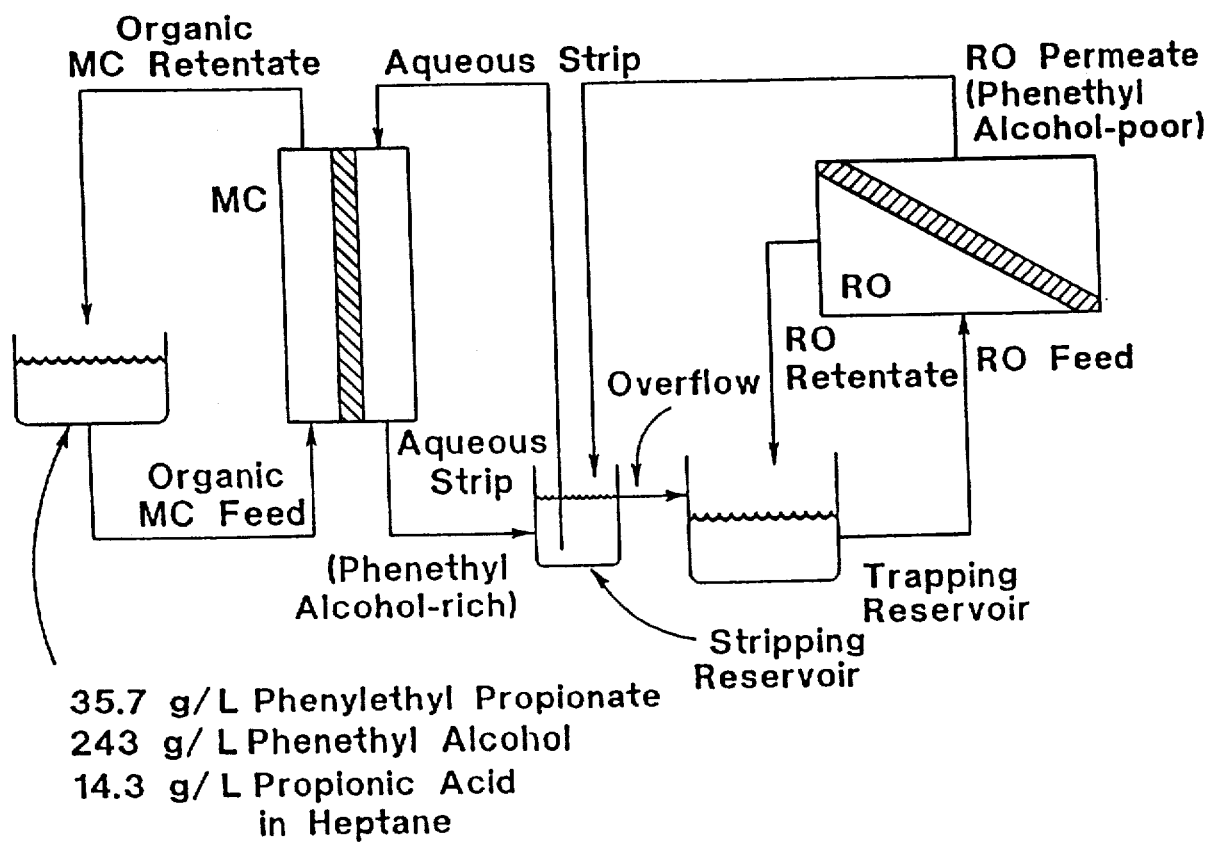

Example 3 was essentially repeated except that the separation was for the products from the enzymatic acylation of (R,S)-phenethyl alcohol as shown in FIG. 13. (The actual enzymatic acylation products of (R,S)-phenethyl alcohol would be (R)-1-phenylethyl propionate and S-phenethyl alcohol and propionic acid; however, since this extraction was to show feasility, racemic mixtures of phenylethyl propionate and phenethyl alcohol were used in the MC feed.) The MC feed contained 35.7 g/L phenylethyl propionate, 24.3 g/L phenethyl alcohol and 14.3 g/L propionic acid in heptane. Two Travenol Laboratory CF 15-11 dialysis modules operating in parallel for a total membrane surface area of 2.2 $m^2$ (23.7 $ft^2$), with a phenethyl alcohol permeability of 0.30 $mg/cm^2.hr.g/L$, were used as membrane contactors. The membrane in the membrane contactors retains the ester (phenylethyl propionate) while allowing the alcohol and the acid to permeate. The RO module, a spiral-wound SW-30 module from FilmTec having a surface area of 2.1 $m^2$ (23 $ft^2$) with a feed flow rate of 7.5 L/min (120 gph) had an average flux of 0.28 $kg/m^2.min$ (10 gph) when driven by a transmembrane pressure of 5514 kPa (800 psi). The organic MC feed flowed on the lumen side at a rate of 1.1 L/min (16.8 gph). The RO permeate had an average flow rate of 0.6 L/min (9.5 gph). Because of the large RO permeate flow, and to allow for fluctuations in the permeate flow, a strip reservoir that acted as a buffer tank was used to ensure a uniform aqueous strip flow. The RO permeate flowed into the strip reservoir where it was combined with the loaded aqueous strip. One exiting stream from the strip reservoir formed the aqueous strip stream, while another exiting stream acted as an overflow, which returned back to the trapping reservoir. The strip reservoir overflow was combined with the RO retentate to form the RO feed. The concentration of phenethyl alcohol in the trapping reservoir rose steadily during the extraction.

The amount of phenethyl alcohol collected in the RO trapping reservoir over the course of 45 minutes, as well as the decrease of phenethyl alcohol in the MC feed, the recovery of phenethyl alcohol from the MC feed and the purity of the feed, defined in the same manner as in Example 3, is shown in the table below.

| | Phenethyl Alcohol Recovery | | | |
|---|---|---|---|---|
| Time (min) | Feed (g) | Product (g) | Feed Purity (%) | Recovery (%) |
| 0 | 17.0 | 0.0 | 60 | 0 |
| 2 | 12.6 | 2.7 | 66 | 16 |
| 4 | 9.4 | 5.9 | 73 | 35 |
| 6 | 6.0 | 9.0 | 81 | 53 |
| 8 | 4.7 | 10.5 | 84 | 62 |
| 10 | 2.8 | 12.7 | 90 | 75 |
| 15 | 1.2 | 14.6 | 95 | 86 |
| 30 | 0.1 | 16.7 | 99.7 | 98 |
| 45 | 0.1 | 16.9 | 99.7 | 99 |

Using the same MC area, MC feed concentrations, and reservoir volumes, the amount of phenethyl alcohol that would be extracted without the use of RO permeate as the aqueous strip was calculated to be as follows:

| | Phenethyl Alcohol Recovery | | | |
|---|---|---|---|---|
| Time (min) | Feed (g) | Product (g) | Feed Purity (%) | Recovery (%) |
| 0 | 17.0 | 0.0 | 60 | 0 |
| 2 | 12.7 | 4.3 | 66 | 25 |
| 4 | 8.8 | 8.2 | 74 | 48 |
| 6 | 6.9 | 10.1 | 78 | 59 |
| 8 | 5.7 | 11.3 | 81 | 66 |
| 10 | 4.6 | 12.4 | 84 | 73 |
| 15 | 3.5 | 13.5 | 88 | 79 |
| 30 | 3.0 | 14.0 | 89 | 82 |
| 45 | 3.0 | 14.0 | 89 | 82 |

As is apparent from the above data, the use of RO permeate as the aqueous strip in accordance with the present invention produces an essentially pure feed and product whereas without the use of the RO membrane separation the feed purity obtained is only 89% with only 82% of the phenethyl alcohol being removed from the feed. Although the feed contained racemic phenylethyl propionate and phenethyl alcohol, the separation achieved showed that enantiomerically pure phenethyl propionate and phenethyl alcohol could be produced from pure mixtures of the same.

EXAMPLE 5

Figure 14:
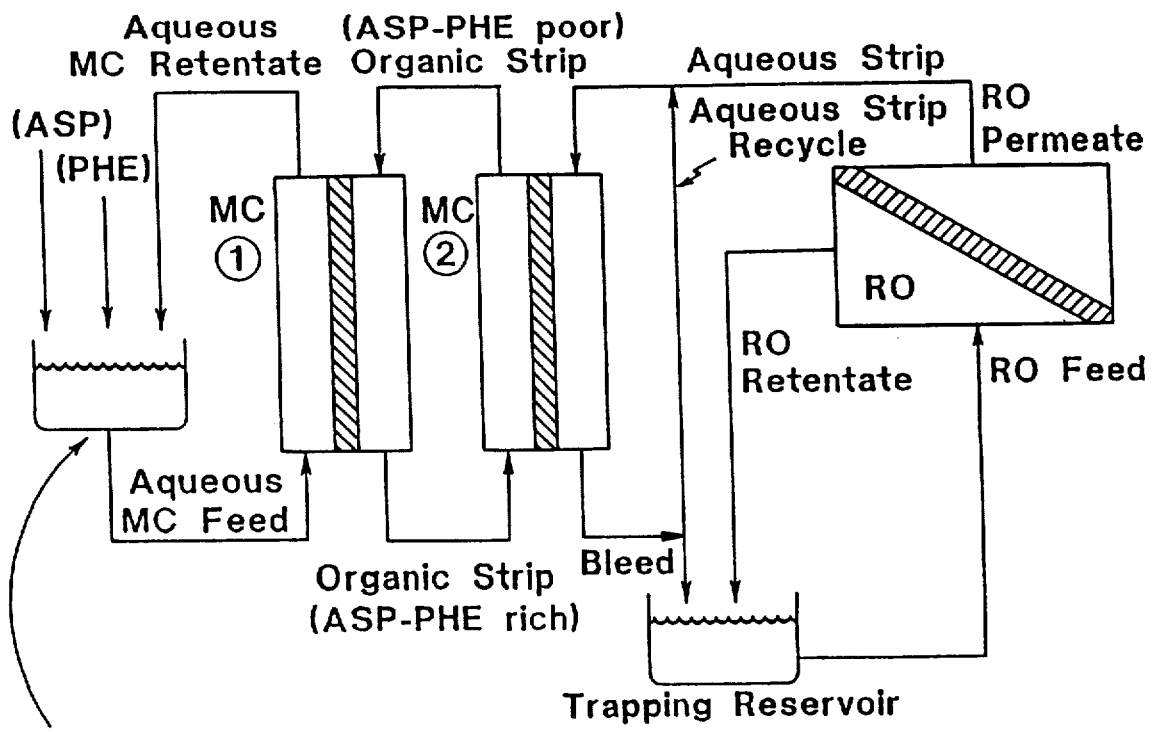

A batch hybrid separation system of the present invention is shown schematically in FIG. 14, comprising two membrane contactors coupled with an RO module, for the recovery of the dipeptide reaction product N-acyl-beta-alkyl ester-L-Asp-L-Phe-alkyl ester (ASP-PHE) from an aqueous enzymatic synthesis reaction solution comprising N-acyl-beta-alkyl ester-L-Asp (ASP) and L-Phe-alkyl ester (PHE). In this system, the two membrane contactors, in addition to serving as extractors, permit recycling of the organic solvent. The membrane contactors comprised modules of Enka B1 cellulose hollow fibers. The first membrane contactor ("MC1") had a surface area of 232 $cm^2$ (0.25 $ft^2$) and acted as the loading module, while the second membrane contactor ("MC2") with a surface area of 465 $cm^2$ (0.50 $ft^2$) acted as the stripping module. The aqueous side of MC1 is fed with an aqueous feed solution containing 1.45 g/L dipeptide (ASP-PHE), together with the other feed constituents, at a rate of 0.3 L/min (4.8 gph) at 101 kPa (14.7 psi). Because of its very low coefficient of partition in water at the feed concentration of 1.45 g/L, the dipeptide in MC1 favors partitioning into the organic phase shown as the right hand side of MC1. This organic phase comprises 75 vol % N,N-diethyldodecanamide and 25 vol % dodecane, and is continuously recycled between the lumen side of MC1 and the lumen side of MC2 at a rate of approximately 10 ml/min (016 gph). In MC2 some partitioning of dipeptide from the recirculating organic phase into the aqueous phase occurs. The extraction water for the aqueous side of MC2 comprises permeate from the RO separator, fed at 25 ml/min (0.4 gph) into a recirculation loop flowing at 0.35 L/min (5.6 gph), for a total flow into the aqueous side of MC2 of 0.38 L/min (6 gph). As shown in FIG. 14, this RO permeate/MC extraction water is continuously recycled through the RO separator. The RO module comprises the same type as in Example 2 having a surface area of 0.93 $m^2$ (10 $ft^2$) with an average flux of 0.027 $kg/m^2.min$ (0.95 gfd) when driven by a TMP of 1206 kPa (175 psi). The feed rate to the RO module was at least 4 L/min (63 gph). Over the course of 64.5 hours, this hybrid system using RO-recycled extraction water yielded a dipeptide concentration in the reservoir of 5.43 g/L. The dipeptide permeability through MC1 and MC2 was 0.13 $mg/cm^2.hr.g/L$. Using the same permeability, reservoir volumes and feed concentrations, the dipeptide concentration in the product reservoir was calculated to be 1.4 g/L without the use of RO-recycled extraction water for the same period of time, or less than one-fourth the yield obtained with the hybrid system.

EXAMPLE 6

Figure 15:
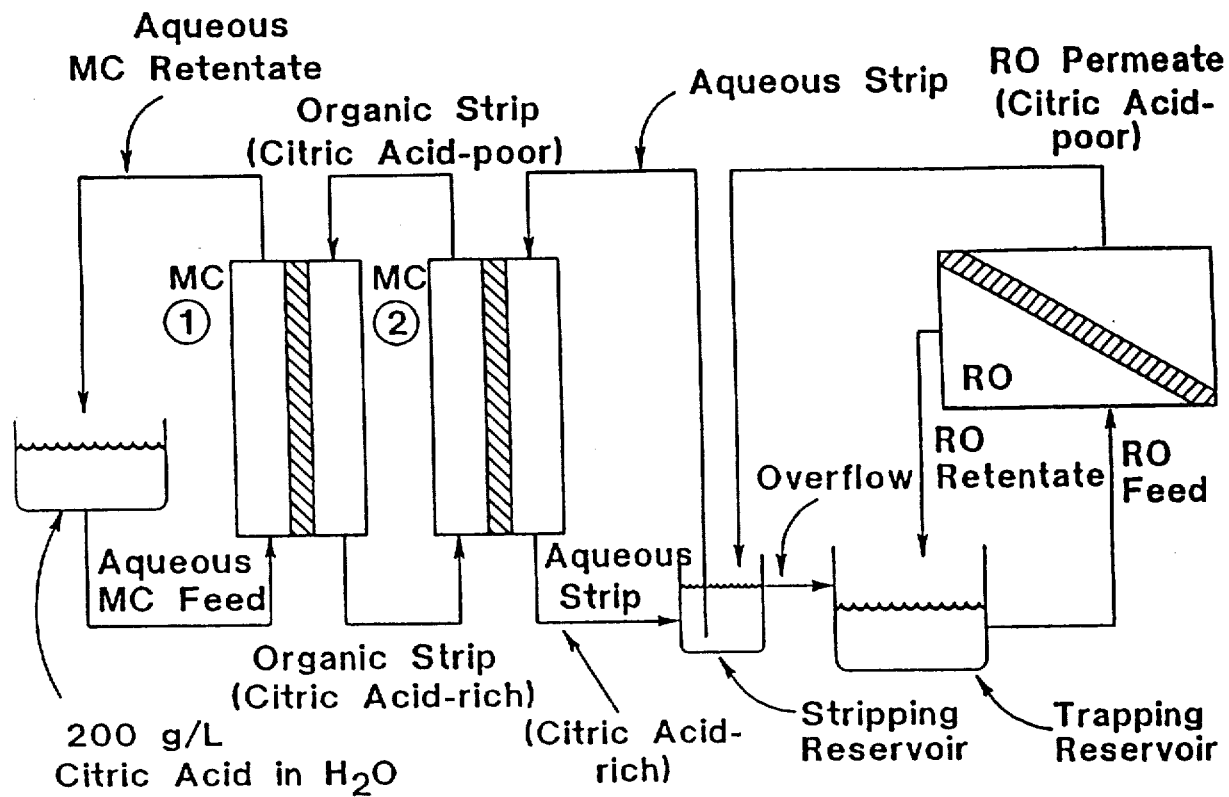

A batch hybrid MC/MC/RO separation system similar to Example 5 is shown schematically in FIG. 15 for the separation of citric acid from fermentation beer. For this particular example, permeabilities obtained from small scale experiments (100 ml feed volume) are used to model a MC/MC/RO separation system that would process one liter of fermentation beer containing 200 g/L citric acid. In this case, one Travenol Laboratory CF 15-11 dialysis module comprises the loading membrane contactor with a membrane surface area of 1.1 $m^2$ (11.8 $ft^2$), while two CF 15-11 dialysis modules comprise the stripping membrane contactors with a combined surface area of 2.2 $m^2$ (23.6 $ft^2$). The RO module is a spiral-wound SW-30 from FilmTec having a membrane surface area of 2.1 $m^2$ (23 $ft^2$. As in Example 5, the two sets of membrane contactors act as extractors as well as allowing recycling of the organic stripping solvent, which in this case is 38 vol % trilaurylamine and 5 vol % N-octanol in Shell Sol 71. The shell side of the loading membrane contactor is fed with the fermentation beer containing 200 g/L citric acid, while the organic stripping solvent circulates between the lumens of the loading and stripping membrane contactors. In FIG. 15, the stripping reservoir acts as a buffer tank. The RC permeate is combined with the loaded aqueous strip in the stripping reservoir. One exiting stream from the stripping reservoir forms the aqueous strip while another exiting stream acts as an overflow and returns to the trapping reservoir where the citric acid is trapped. The citric acid, because of its high coefficient of partition into the organic strip permeates the loading membrane contactor with a permeability of 0.18 mg/cm$^2$.hr.g/L. The now-loaded organic strip, so designated because of the considerably increased concentration of citric acid, is circulated to the lumen side of the stripping membrane contactors whereby it is stripped of the citric acid by the citric acid-poor aqueous strip. The stripping permeability in this case is the same as the loading permeability. The RO module yields an average flux of 0.43 kg/m$^2$.min (15.3 gfd) under a TMP of 5514 kPa (800 psi). The table below shows the calculated results when RO permeate is used for the aqueous strip.

| | | Citric Acid Extraction | | |
|---|---|---|---|---|
| Time (hr) | Feed (g) | Organic (g) | Product (g) | Recovery (%) |
| 0.0 | 200 | 0 | 0 | 0 |
| 0.5 | 94 | 61 | 44 | 22 |
| 1.0 | 48 | 42 | 109 | 55 |
| 2.0 | 19 | 18 | 163 | 82 |
| 3.0 | 8 | 8 | 184 | 92 |
| 4.0 | 3 | 3 | 193 | 97 |
| 5.0 | 2 | 2 | 196 | 98 |
| 6.0 | 1 | 1 | 197 | 99 |

Using the same surface areas and permeabilities for the loading and stripping membrane contactors and the same reservoir volumes, the amount of citric acid extractable from the feed without the use of RO permeate serving as the aqueous strip was calculated and is noted in the table below.

| | | Citric Acid Extraction | | |
|---|---|---|---|---|
| Time (hr) | Feed (g) | Organic (g) | Product (g) | Recovery (%) |
| 0.0 | 200 | 0 | 0 | 0 |
| 0.5 | 94 | 65 | 40 | 20 |
| 1.0 | 58 | 63 | 79 | 40 |
| 2.0 | 34 | 56 | 110 | 55 |
| 3.0 | 30 | 54 | 116 | 58 |
| 4.0 | 29 | 54 | 117 | 59 |
| 5.0 | 29 | 54 | 117 | 59 |
| 6.0 | 29 | 54 | 117 | 59 |

As is apparent, the use of RO permeate as the aqueous strip in accordance with the present invention removes virtually all of the citric acid in the fermentation beer and recovers 99% of the citric acid in the trapping reservoir, whereas without RO, the citric acid removal essentially stops after only three hours with only 86% of the critic acid being removed from the feed, while recovering only 59% of the citric acid in the strip reservoir. (The remaining citric acid is retained in the organic extractant.)

EXAMPLE 7

Figure 16:
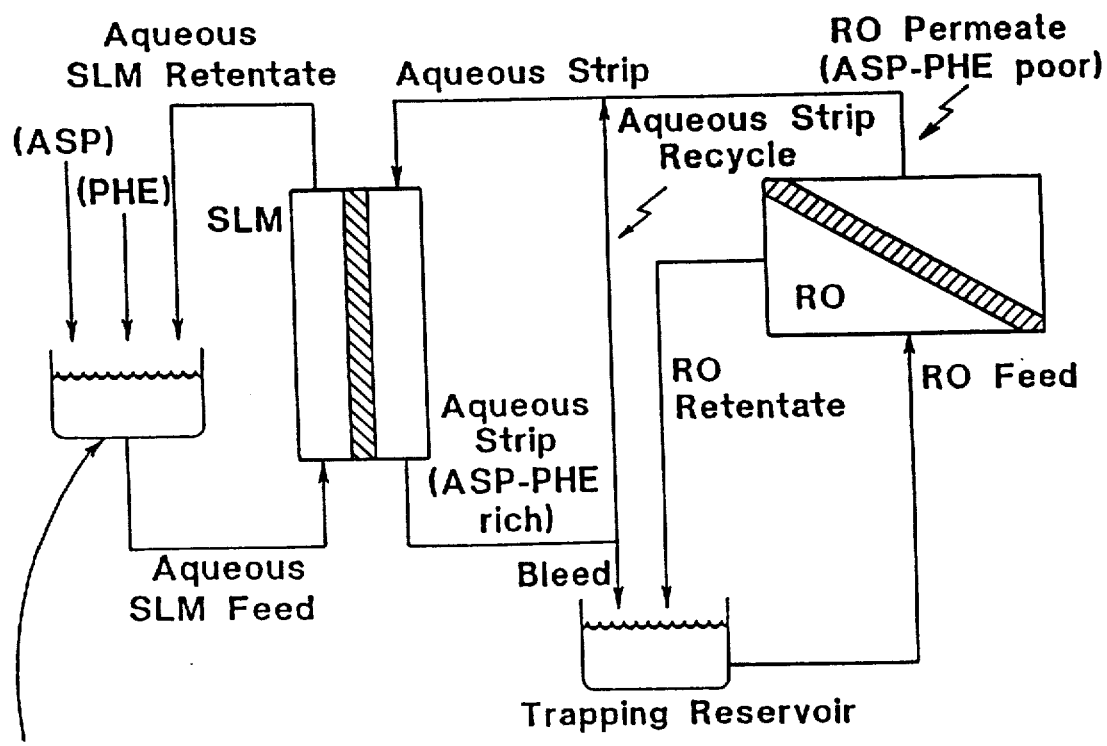

A batch hybrid SLM/RO separation system is shown schematically in FIG. 16 for the extraction of the dipeptide reaction product ASP-PHE from the enzymatic synthesis reaction of Example 5. Using the same scale as Example 5 for the volumes, areas, concentrations and permeabilities that were obtained in small-scale SLM experiments (100 cm$^3$ feed volume), the dipeptide concentration of the product reservoir was calculated when RO-recycled extraction water is used and when not. In this Example, although the feed is aqueous, extraction of the desired organic solute is nevertheless from an organic solvent (the organic solvent is present in the pores of the SLM) by water. The SLM is a hollow fiber module containing Celgard X-20 fibers with a surface area of 0.047 m$^2$ (0.5 ft$^2$) with the fiber walls wetted by 75 vol % N,N-diethyldodecanamide and 25 vol % dodecane The RO module is a FilmTec SW-30 with a surface area of 0.93 m$^2$ (10 ft$^2$) with an average flux of 0.07 kg/m$^2$.min (2.49 gfd) when driven by a TMP of 1206 kPa (175 psi). The permeability of the SLM to dipeptides was 0.38 mg/cm$^2$.hr.g/L. As in Example 5, the RO permeate was combined with the aqueous strip recycle to form the aqueous strip entering the aqueous side of the SLM. A bleed stream from the aqueous strip after it leaves the SLM flows into the trapping reservoir where it is then combined with the dipeptide-rich RO retentate. These combined streams form the RO feed. The calculated amounts of dipeptide in the trapping reservoir when extracted with and without RO-recycled extraction water is shown in the table below.

| | Dipeptide Recovery | |
|---|---|---|
| Time (hr) | With RO (g) | Without RO (g) |
| 0 | 0 | 0 |
| 0.8 | 0.2 | 0.2 |
| 2.4 | 0.6 | 0.5 |
| 4.8 | 1.2 | 0.9 |
| 8.0 | 1.9 | 1.2 |
| 16.0 | 3.8 | 1.4 |
| 20.0 | 4.7 | 1.6 |
| 24.0 | 5.6 | 1.7 |
| 28.0 | 6.2 | 1.7 |
| 30.0 | 6.3 | 1.7 |

As is apparent from the above, the use of RO-recycled extraction water in accordance with the present invention produces roughly a four-fold increase in dipeptide recovery.

EXAMPLE 8

Figure 17:
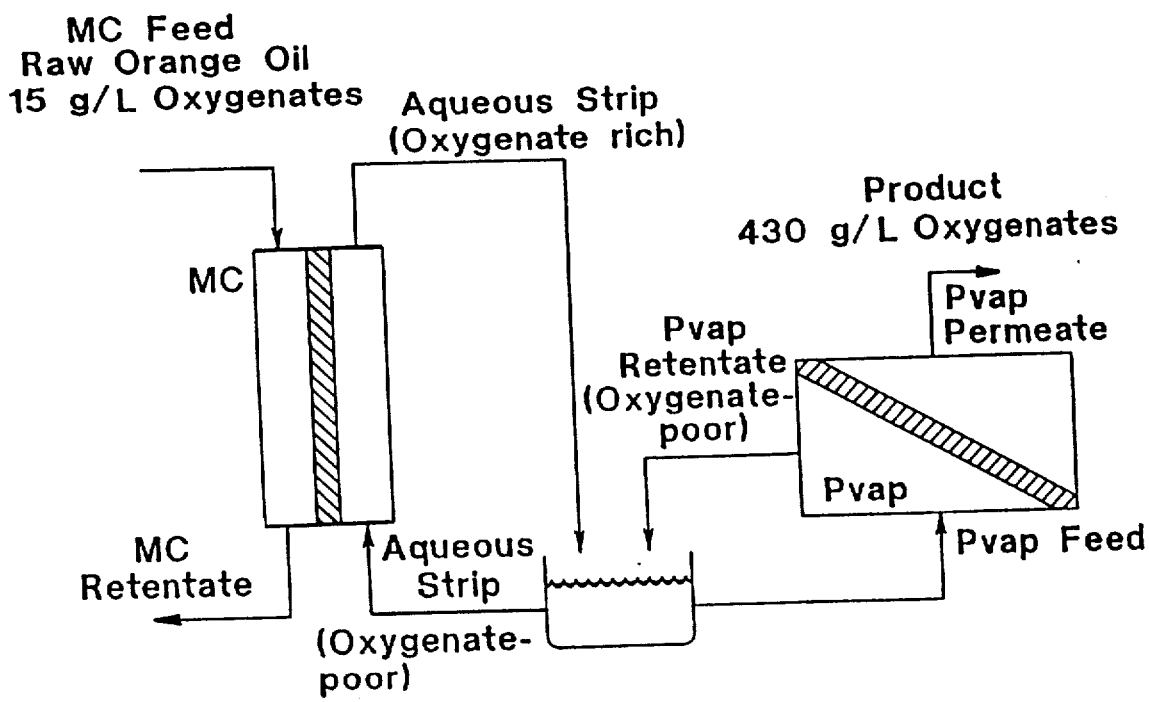

A continuous hybrid MC/Pvap separation system is shown schematically in FIG. 17, for the extraction of orange oil oxygenates from orange oil containing 15 g/L oxygenates. Two Travenol CF 15-11 membrane contactors with a total area of 2.2 m$^2$ (23.7 ft$^2$) had a feed flow rate of 0.4 L/min (6.4 gph) at 138 kpa (20 psia). The permeability of the membrane contactors to oxygenates was $6.0 \times 10^{-3}$ mg/cm$^2$.hr.g/L, while its oxygenates flux was 0.042 mg/cm$^2$.hr. Continuously recycled extraction water was fed to the aqueous side of the MCs at a rate of 2.0 L/min (31.8 gph). The Pvap separator was a flat sheet Pebax 3533 membrane from Atochem having a surface area of $1.82 \times 10^{-2}$ m$^2$ (0.2 ft$^2$) having an oxygenates flux of 0.11 mg/cm$^2$.hr and a water flux of 36.9 mg/cm$^2$.hr, all at a temperature of 45° C. and a permeate pressure of 2.55 kPa (0.025 psi). The Pvap retentate, largely comprising water and a small amount of oxygenates, is fed to the reservoir where it is combined with the oxygenates-rich extraction water from the MC and then either recycled to the aqueous side of the MC or fed as the feed to the Pvap separation unit. The Pvap permeate, which flows at the rate of 0.12 ml/min (0.002 gph), comprises a two-phase permeate stream, of which the oil phase contains 430 g/L oxygenates. The same system was run without the Pvap separator with the same feed, to yield an aqueous product containing 0.023 g/L oxygenates—a 20,000-fold lower concentration than was obtained using the hybrid MC/Pvap system.

EXAMPLE 9

Figure 18:
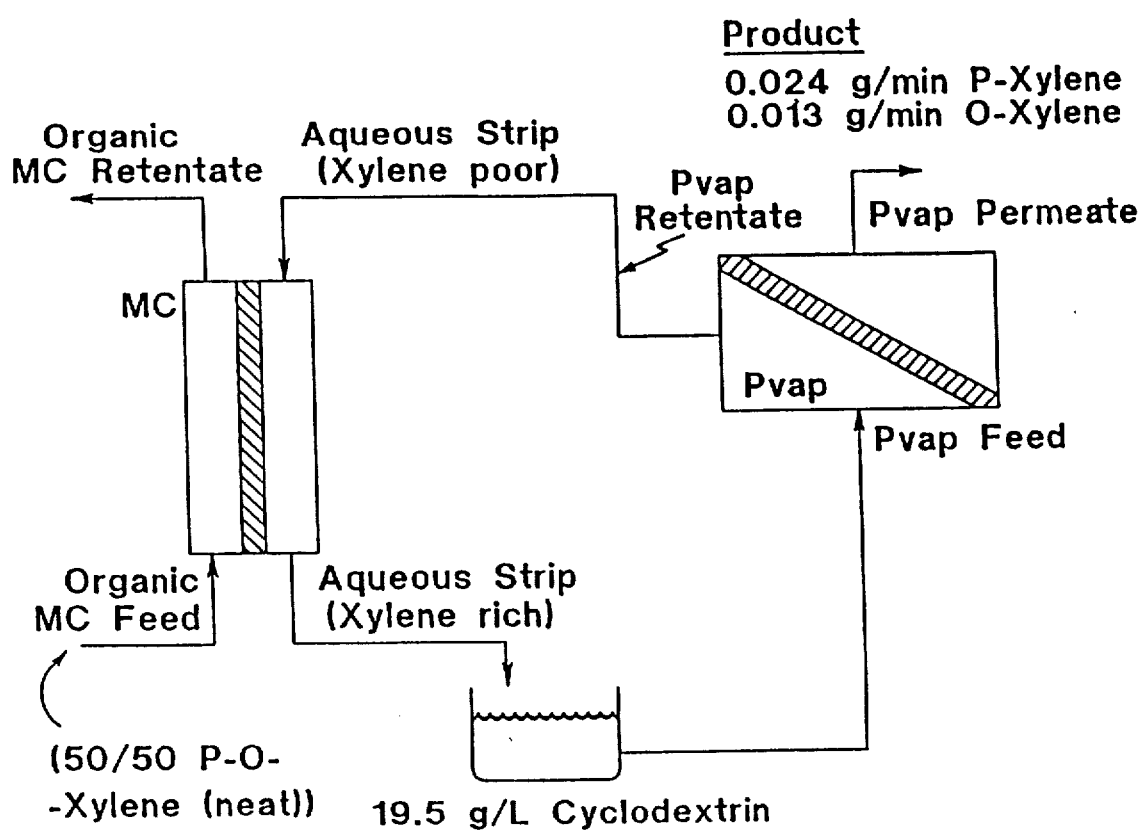

A continuous hybrid MC/Pvap separation system is shown schematically in FIG. 18, for the extraction of para-xylene from a feed comprising para-xylene in an organic solvent. The membrane contactor comprised Celgard X-20 hollow fibers with a total surface area of 0.093 m$^2$ (1.0 ft$^2$), the organic side of which was fed at the rate of 0.2 L/min (3.2 gph) at atmospheric pressure and 30° C. The aqueous side of the membrane contactor was fed Pvap retentate water at 0.5 L/min (8.0 gph), the water containing 19.5 g/L cyclodextrin as a water-soluble, para-xylene-specific complexing agent. The MC had a para-xylene flux of 1.55 mg/cm$^2$.hr. The Pvap module, comprising squalane-wetted Celgard X-20 hollow fibers with a surface area of 0.14 m$^2$ (1.5 ft$^2$), yielded a para-xylene flux of 1.03 mg/cm$^2$.hr. The permeate pressure for the Pvap module was 0.67 kPa (0.1 psi). The hybrid separation system was run for more than six hours and the Pvap permeate yielded the amounts of para-xylene noted below.

| p-Xylene Recovery in Pvap Permeate | |
|---|---|
| Time (min) | p-Xylene (g) |
| 0 | 0.0 |
| 74 | 2.3 |
| 160 | 3.3 |
| 195 | 4.3 |
| 234 | 6.0 |
| 304 | 7.4 |
| 364 | 8.8 |

The same system was operated on the same feed at the same conditions without the Pvap separator. The aqueous strip essentially reached equilibrium after only one hour, yielding significantly lower amounts of para-xylene, as shown below. As is apparent, significantly greater amounts of the organic solute can be recovered when a Pvap separation system is combined with the MC separation system in accordance with the present invention.

| Xylene Recovery in Aqueous Reservoir | |
|---|---|
| Time (min) | p-Xylene (g) |
| 0 | 0.00 |
| 7 | 0.15 |
| 15 | 0.23 |
| 30 | 0.28 |
| 45 | 0.30 |
| 60 | 0.31 |

EXAMPLE 10

Figure 19:
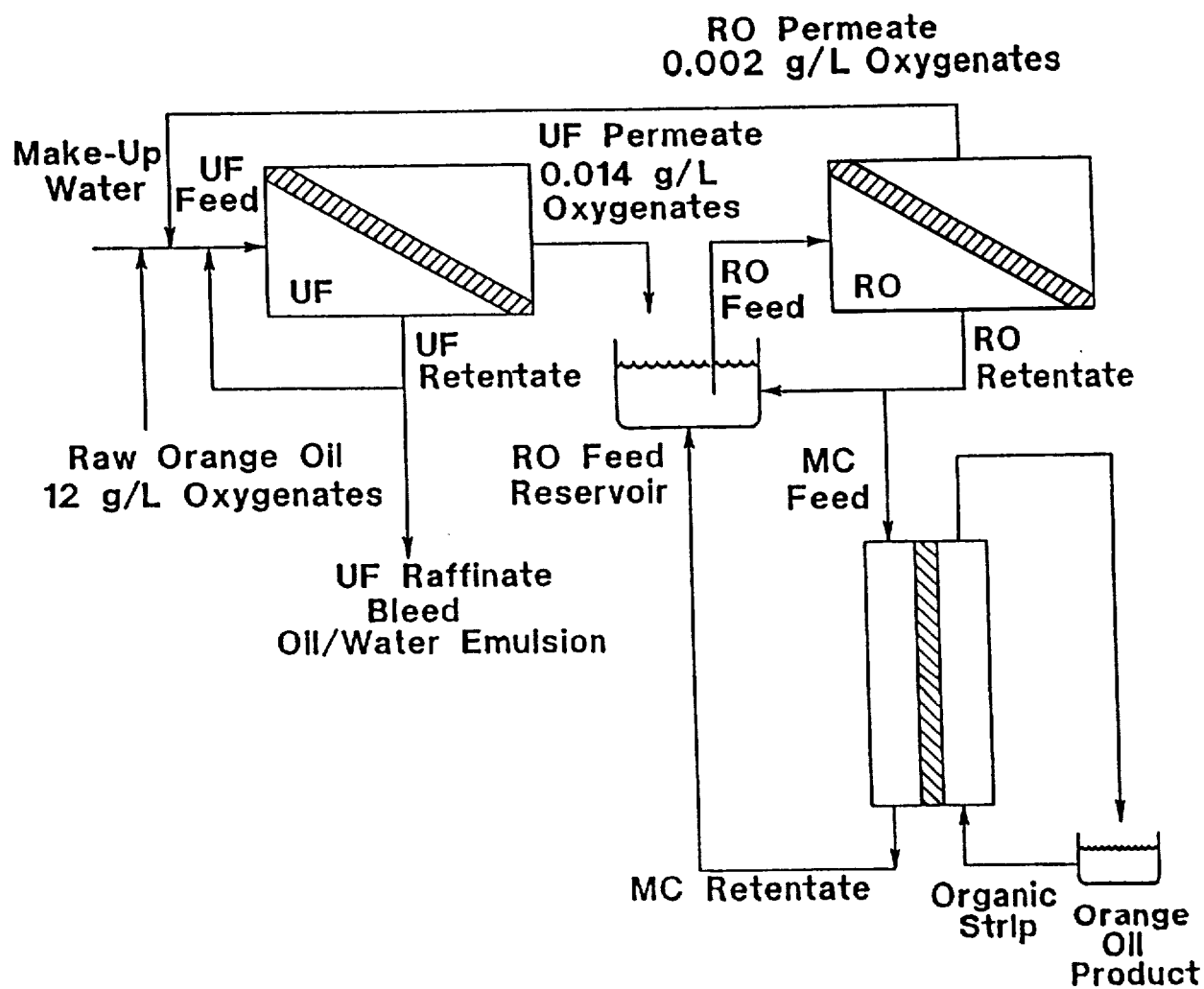

A batch hybrid UF/RO/MC separation system of the present invention is shown schematically in FIG. 19 for the separation of oxygenates from the solvent orange oil, the product comprising orange oil enriched in oxygenates. This system combines RO as the trapping mechanism and membrane contactors as the tapping mechanism. The UF membrane comprised a tubular ACN 620 module from Patterson Candy having a surface area of 0.45 m$^2$ (4.84 ft$^2$) with a lumen side feed and a flux of 0.89 kg/m$^2$.min (31.9 gfd) when driven by a TMP of 414 kPa (60 psi). The RO module was a Patterson Candy AFC 99 module containing 0.9 m$^2$ (9.7 ft$^2$) of membrane with a flux of 0.17 kg/m$^2$.min (5.9 gfd) when driven by a TMP of 3791 kPa (550 psi). The raw orange oil, containing 12 g/L oxygenates, was fed at a rate of approximately 3 ml/min (0.05 gph) and combined with make-up water flowing at 29 ml/min (4.6 gph), RO permeate flowing at 150 ml/min (2.4 gph) and recycled UF retentate to form the UF feed, a 7% oil/water emulsion, for a total flow of 20 L/min (317 gph). A 40 ml/min (0.63 gph) stream comprising an oil/water emulsion also containing approximately 7% oil made up the UF retentate bleed. The UF permeate, containing approximately 0.014 g/L oxygenates, was combined in the RO reservoir along with the RO retentate and MC retentate. A bleed stream from the RO retentate containing approximately 0.22 g/L oxygenates comprised the feed to the MC, comprising a module of 0.046 m$^2$ (0.5 ft$^2$) Enka B1 cellulose fibers, while the orange oil product acted as the organic strip, thereby becoming enriched in oxygenates. Since the RO membrane retained oxygenates while allowing water to permeate, the RO retentate stream was thereby enriched in oxygenates. This concentrated oxygenate stream was fed, via the RO retentate bleed, to the MC where oxygenates permeated the membrane and were recovered in the orange oil product stream. The MC retentate being depleted in oxygenates has the effect of reducing the oxygenate concentration in the RO reservoir, thereby maintaining a constant RO permeat flow and eliminating the need for a bleed-and-feed step when the oxygenate concentration gets too high.

The amount of oxygenates in the 25 ml orange oil product over the course of 66 hours is shown in the table below.

| Oxygenate Recovery in Orange Oil Product | | |
|---|---|---|
| Time (hr) | Oxygenates (g) | Oxygenate Concentration (g/L) |
| 0 | 0.34 | 13.6 |
| 4.8 | 0.58 | 23.2 |
| 21.8 | 0.85 | 34.0 |
| 28.8 | 0.91 | 36.4 |
| 42.8 | 1.10 | 44.0 |
| 53.3 | 1.19 | 47.6 |
| 66.0 | 1.30 | 52.0 |

As is apparent, the use of this UF/RO/MC system in accordance with the present invention allows the extraction of an organic solute from an organic solvent using water and also allows a means of recovering the organic solute from the aqueous extract. The form of the trapping mechanism used in this Example also benefits the system by requiring no make-up water whereas an ordinary feed and bleed on the trapping reservoir would require the use of make-up water.

EXAMPLE 11

Figure 20:
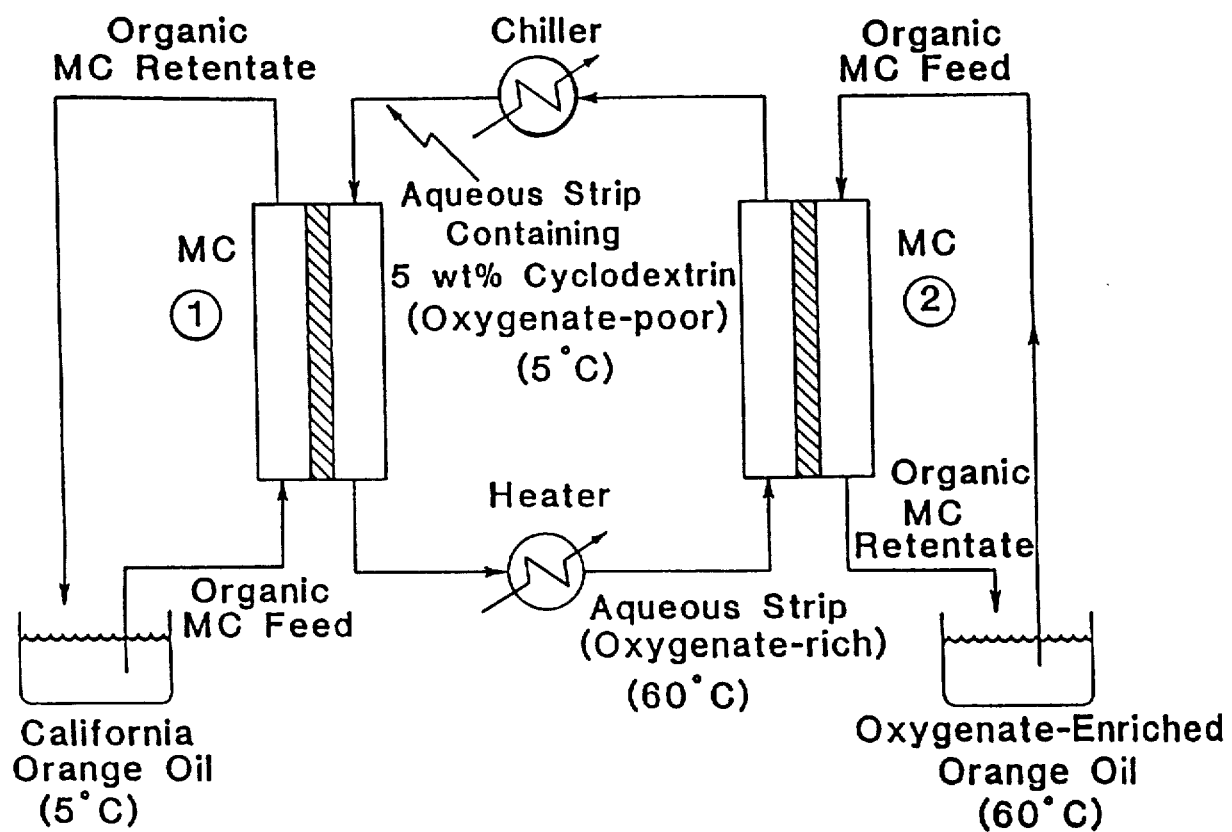

A batch hybrid MC/MC separation system is shown schematically in FIG. 20, also for the extraction of oxygenates from the solvent orange oil. Both MCs were hollow fiber CF 15-11 dialysis modules, with a surface area of 1.1 m² (11.8 ft²) in each module. Raw California orange oil (1.5 L) containing 12 g/L oxygenates was circulated through the lumens of the first MC at 5° C. and at a flow rate of 0.30 L/min (4.8 gph); an aqueous solution (2.0 L) containing 5 wt % cyclodextrin as a water-soluble oxygenate-specific complexing agent was circulated through the shell side of the first MC at 5° C. and 0.20 L/min (3.2 gph), and through the shell side of the second MC at 60° C. and 0.20 L/min (3.2 gph); and a product orange oil solution (0.125 L) was circulated through the lumens of the second MC at 60° C. and 0.30 L/min (4.8 gph). Oxygenates from the raw orange oil permeated the first MC at 5° C. with a permeability of 0.08 mg/cm².hr.g/L, resulting in enrichment of the cold aqueous strip solution. This loaded strip solution was heated to 60° C. and fed to the second MC (also at 60° C.), where the oxygenates permeated the MC with a permeability of 0.77 mg/cm².hr.g/L, resulting in enrichment of the product orange oil. Operation of the two MCs at different temperatures resulted in the net transport of oxygenates from the feed orange oil to the product orange oil, resulting in the effective trapping of oxygenates in the product orange oil. The maximum concentration of oxygenates attained in the product orange oil was 62.4 g/L.

The system was run without the second MC to trap oxygenates, and the maximum concentration of oxygenates attained in the aqueous strip solution (containing 5 wt % cyclodextrin) was 0.50 g/L—a 125-fold lower concentration than was obtained using the hybrid MC/MC system.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. In an organic/aqueous extraction process for the extraction of an organic solute from an organic solvent or solvent mixture with an aqueous-based extractant, the improvement comprising continuously recycling said aqueous-based extractant through a membrane separation process that selectively removes said organic solute from said aqueous-based extractant, said membrane separation process being selected from at least one of reverse osmosis, nanofiltration, ultrafiltration, membrane distillation, pervaporation, membrane contactor and supported-liquid membrane.

2. The process of claim 1 wherein said aqueous-based extractant is from a membrane separation process in which organic-solute-poor water permeates the membrane.

3. The process of claim 2 wherein said membrane separation process is selected from at least one of reverse osmosis, nanofiltration, ultrafiltration, and membrane distillation.

4. The process of claim 1 wherein said aqueous-based extractant is from a membrane separation process in which organic-solute-poor water is recovered as the retentate to said membrane separation process.

5. The process of claim 4 wherein said membrane separation process is selected from at least one of pervaporation, membrane contactor, and supported-liquid membrane.

6. The process of claim 1 wherein said organic/aqueous extraction process is selected from the processes of conventional liquid extraction, ultrafiltration, membrane contactors, supported-liquid membranes, and combinations thereof.

7. The process of claim 1 wherein said organic/aqueous extraction process comprises conventional liquid extraction.

8. The process of claim 7 wherein said membrane separation process comprises reverse osmosis.

9. The process of claim 7 wherein said membrane separation process comprises a membrane contactor.

10. The process of claim 7 wherein said membrane separation process comprises membrane distillation.

11. The process of claim 7 wherein said membrane separation process comprises nanofiltration.

12. The process of claim 7 wherein said membrane separation process comprises ultrafiltration.

13. The process of claim 7 wherein said membrane separation process comprises pervaporation.

14. The process of claim 1 wherein said organic/aqueous extraction process comprises ultrafiltration.

15. The process of claim 14 wherein said membrane separation process comprises reverse osmosis.

16. The process of claim 15 wherein said membrane separation process additionally comprises a membrane contactor.

17. The process of claim 14 wherein said membrane separation process comprises pervaporation.

18. The process of claim 14 wherein said membrane separation process comprises a membrane contactor.

19. The process of claim 14 wherein said membrane separation process comprises membrane distillation.

20. The process of claim 14 wherein said membrane separation process comprises nanofiltration.

21. The process of claim 1 wherein said organic/aqueous extraction process comprises a membrane contactor.

22. The process of claim 21 wherein said membrane separation process comprises reverse osmosis.

23. The process of claim 22 wherein said organic solute comprises R-Norbornenol.

24. The process of claim 22 wherein said organic solute comprises phenethyl alcohol.

25. The process of claim 21 wherein said membrane separation process comprises pervaporation.

26. The process of claim 25 wherein said organic solute comprises para-xylene.

27. The process of claim 21 wherein said membrane separation process comprises a membrane contactor.

28. The process of claim 21 wherein said organic solute comprises orange oil oxygenates.

29. The process of claim 21 wherein said membrane separation process comprises a supported-liquid membrane.

30. The process of claim 21 wherein said membrane separation process comprises membrane distillation.

31. The process of claim 21 wherein said membrane separation process comprises nanofiltration.

32. The process of claim 1 wherein said organic/aqueous extraction process comprises a supported-liquid membrane.

33. The process of claim 32 wherein said membrane separation process comprises reverse osmosis.

34. The process of claim 33 wherein said organic solute comprises the dipeptide N-acyl-beta-alkyl ester-L-Asp-L-Phe-alkyl ester.

35. The process of claim 32 wherein said membrane separation process comprises pervaporation.

36. The process of claim 32 wherein said membrane separation process comprises a membrane contactor.

37. The process of claim 32 wherein said membrane separation process comprises membrane distillation.

38. The process of claim 32 wherein said membrane separation process comprises nanofiltration.

39. The process of claim 1 wherein said organic-/aqueous extraction process comprises two membrane contactors.

40. The process of claim 39 wherein said membrane separation process comprises reverse osmosis.

41. The process of claim 40 wherein said organic solute comprises the dipeptide N-acyl-beta-alkyl ester-L-Asp-L-Phe-alkyl ester.

42. The process of claim 40 wherein said organic solute comprises citric acid.

43. The process of claim 39 wherein said membrane separation process comprises pervaporation.

44. The process of claim 39 wherein said membrane separation process comprises membrane distillation.

45. A continuous pressure-driven membrane separation process for the selective extraction of essential oil oxygenates from essential oils comprising contacting a feed stream comprising water and essential oil with an ultrafiltration membrane, collecting an oxygenates-rich permeate from said ultrafiltration membrane and combining said permeate with the retentates from a membrane contactor and from a reverse osmosis membrane to form a combined feed to said reverse osmosis membrane, contacting said combined feed with said reverse osmosis membrane, recycling an oxygenates-poor aqueous permeate from said reverse osmosis membrane to said feed stream, supplying a portion of said retentate from said reverse osmosis membrane as a membrane contactor feed to said membrane contactor, contacting said membrane contactor feed with said membrane contactor, and recovering concentrated essential oil oxygenates from the permeate of said membrane contactor.

46. A continuous pressure-driven membrane separation process for the selective extraction of essential oil oxygenates from essential oils comprising contacting a feed stream comprising an essential oil with one side of a first membrane contactor, contacting the other side of said first membrane contactor with water, collecting an oxygenates-rich permeate from said first membrane contactor and combining said permeate with the retentates from a second membrane contactor and a reverse osmosis membrane to form a combined feed to said reverse osmosis membrane, contacting said combined feed with said reverse osmosis membrane, recycling an oxygenates-poor aqueous permeate from said reverse osmosis membrane to said feed stream, supplying a portion of said retentate from said reverse osmosis membrane as a feed to said second membrane contactor, contacting said second membrane contactor feed with said second membrane contactor, and recovering concentrated essential oil oxygenates from the permeate of said second membrane contactor.

47. A continuous pressure-driven membrane separation process for the selective extraction of essential oil oxygenates from essential oils comprising contacting a feed stream comprising an essential oil with one side of a membrane contactor, contacting the other side of said membrane contactor with an aqueous strip stream, collecting an oxygenates-rich permeate from said membrane contactor, contacting said oxygenates-rich permeate with a pervaporation membrane, recovering concentrated essential oil oxygenates from the permeate of said pervaporation membrane, and continuously recycling the aqueous retentate of said pervaporation membrane as said aqueous strip stream.

48. The process of claim 45, 46 or 47 wherein said oxygenates are selected from alcohols, aldehydes, ketones, and esters.

49. The process of claim 45, 46 or 47 wherein said essential oil is selected from cold-pressed and distilled citrus oil.

50. The process of claim 49 wherein said citrus oil is selected from orange oil, lemon oil, lime oil and grapefruit oil.

51. An oxygenates-enriched essential oil composition produced by the process of claim 45, 46 or 47.

* * * * *

UNITED STATES PATENT AND TRADEMARK OFFICE
CERTIFICATE OF CORRECTION

PATENT NO. : 5,041,227

DATED : August 20, 1991

INVENTOR(S) : Paul van Eikeren et al

It is certified that error appears in the above-identified patent and that said Letters Patent is hereby corrected as shown below:

INCLUDE FIGS. 3-20 of the drawings (copies enclosed)

Col. 6, Line 37: Change "2.2 x 10" to -- $2.2 \times 10^{-3}$ --.

Col. 7, Line 46: Change "rin" to -- min --.

Col. 10, Line 63: Add -- ) -- after "$ft^2$".

Col. 12, Line 55: Change "kpa" to -- kPa --.

Signed and Sealed this

Sixteenth Day of February, 1993

*Attest:*

STEPHEN G. KUNIN

*Attesting Officer*   Acting Commissioner of Patents and Trademarks 102.6 g/L N-acyl-β-Alkyl ester-L-ASP (ASP)
72.3 g/L L-Phe-Alkyl ester (PHE)
42 g/L enzyme
1.45 g/L Aspartyl-Phenylalanine dipeptide (ASP-PHE)

102.6 g/L N-acyl-B-Alkyl ester-L-ASP (ASP)
72.3 g/L L-Phe-Alkyl ester (PHE)
42 g/L enzyme
1.45 g/L Aspartyl-Phenylalanine
dipeptide (ASP-PHE)